United States Patent
Borriello et al.

(10) Patent No.: US 9,120,824 B2
(45) Date of Patent: Sep. 1, 2015

(54) CYCLIC AMINE DERIVATIVES AS $EP_4$ RECEPTOR AGONISTS

(75) Inventors: Manuela Borriello, Monza (IT); Sabrina Pucci, Bernareggio (IT); Luigi Piero Stasi, Monza (IT); Lucio Rovati, Monza (IT)

(73) Assignee: ROTTAPHARM BIOTECH S.R.L., Monza (IT)

( * ) Notice: Subject to any disclaimer, the term of this patent is extended or adjusted under 35 U.S.C. 154(b) by 0 days.

(21) Appl. No.: 14/127,474

(22) PCT Filed: Jul. 4, 2011

(86) PCT No.: PCT/EP2011/061229
§ 371 (c)(1),
(2), (4) Date: May 5, 2014

(87) PCT Pub. No.: WO2013/004291
PCT Pub. Date: Jan. 10, 2013

(65) Prior Publication Data
US 2014/0243373 A1    Aug. 28, 2014

(51) Int. Cl.
*C07F 1/02* (2006.01)
*C07D 207/16* (2006.01)
*C07D 211/60* (2006.01)

(52) U.S. Cl.
CPC ............ *C07F 1/02* (2013.01); *C07D 207/16* (2013.01); *C07D 211/60* (2013.01)

(58) Field of Classification Search
None
See application file for complete search history.

(56) References Cited

FOREIGN PATENT DOCUMENTS

WO    2008092860    8/2008

OTHER PUBLICATIONS

International Search Report dated Sep. 22, 2011 corresponding to PCT/EP2011/061229; 4 pages.
Written Opinion dated Sep. 22, 2011 corresponding to PCT/EP2011/061229; 4 pages.

*Primary Examiner* — Timothy R Rozof
(74) *Attorney, Agent, or Firm* — Ohlandt Greeley Ruggiero & Perle L.L.P.

(57) ABSTRACT

There is described a group of novel cyclic amine derivative compounds having an $EP_4$ receptor agonistic activity.
Specifically, the compounds according to the invention are provided with analgesic, antinflammatory, antiglaucoma activity, and also with anti-osteoporosis and antiulcerative activity.
The present invention therefore relates to novel cyclic amine derivative compounds, processes for their preparation, pharmaceutical compositions containing them and their use as medicaments, inter alia for the treatment or alleviation of Prostaglandin E mediated diseases such as pain, glaucoma, ulcerative colitis and osteoporosis.

11 Claims, No Drawings

CYCLIC AMINE DERIVATIVES AS EP$_4$ RECEPTOR AGONISTS

FIELD OF THE INVENTION

The present invention relates to novel cyclic amine derivative compounds, processes for their preparation, pharmaceutical compositions containing them and their use as medicaments, inter alia for the treatment or alleviation of Prostaglandin E mediated diseases such as pain, glaucoma, ulcerative colitis and osteoporosis.

BACKGROUND OF THE INVENTION

A number of review articles describe the characterization and therapeutic relevance of the prostanoid receptors as well as the most commonly used selective agonists and antagonists; *Eicosanoids: From Biotechnology to therapeutic Applications*, Folco, Samuelson, Maclouf and Velo eds, Plenum Press, New York, 1996, chap. 14, 137-154; *"Molecular aspects of the structures and functions of the prostaglandin E receptors"*, Journal of Lipid Mediators and Cell Signalling, 1996, 14, 83-87; *"Function of prostanoid receptors: studies on knockout mice"*, Prostaglandins & other Lipid Mediators, 2002, 68-69, 557-573 and *"Prostanoid receptor antagonists: development strategies and therapeutic applications"*, British Journal of Pharmacology (2009), 158, 104-145. Prostaglandin E2 (PGE$_2$) is a member of the prostanoid family with a variety of physiological effects, including mucosal protection, induction of gastric acid secretion in stomach, generation of fever, hyperalgesia, inflammation and immunity. These actions of PGE$_2$ are mediated by four G-protein-coupled PGE$_2$ receptors, EP$_1$, EP$_2$, EP$_3$ and EP$_4$.

The EP$_4$ receptor is a 7-transmembrane receptor whose activation is normally associated with elevation of intracellular cyclic adenosine monophosphate (cAMP) levels. PGE$_2$-activated EP$_4$ receptor signalling may be involved in various pathologic states, such as pain (in particular inflammatory, neuropathic and visceral), inflammation, neuroprotection, cancer, dermatitis, bone disease, immune system dysfunction promotion of sleep, renal regulation, gastric or enteric mucus secretion and duodenal bicarbonate secretion.

In The Journal of Immunology (2008) 181, 5082-5088, studies suggest that PGE$_2$ inhibits proteoglycan synthesis and stimulates matrix degradation in osteoarthritic chondrocytes via the EP$_4$ receptor. Targeting EP$_4$, rather than cyclooxygenase 2, could represent a future strategy for osteoarthritis disease modification.

In European Journal of Pharmacology (2008) 580, 116-121, studies suggest that a pharmacological blockade of the prostanoid EP$_4$ receptor may represent a new therapeutic strategy in signs and symptomatic relief of osteoarthritis and/or rheumatoid arthritis.

A number of publications have demonstrated that PGE$_2$ acting through the EP$_4$ receptor subtype, and EP$_4$ agonists alone, can regulate inflammatory cytokines after an inflammatory stimulus. Takayama et al in the Journal of Biological Chemistry (2002) 277, 46, 44147-54, showed that PGE$_2$ modulates inflammation during inflammatory diseases by suppressing macrophage derived chemokine production via the EP$_4$ receptor. In Bioorganic & Medicinal Chemistry (2002) 10, 7, 2103-2110, Maruyama et al demonstrate the selective EP$_4$ receptor agonist ONO-AE1-437 suppresses LPS induced TNF-a in human whole blood whilst increasing the levels of IL-10. An article from Anesthesiology, (2002) 97, 170-176, suggests that a selective EP$_4$ receptor agonist ONO-AE1-329 effectively inhibited mechanical and thermal hyperalgesia and inflammatory reactions in acute and chronic monoarthritis.

Two independent articles from Sakuma et al in Journal of Bone and Mineral Research (2000) 15, 2, 218-227 and Miyaura et al in Journal of Biological Chemistry (2000) 275, 26, 19819-23, report impaired osteoclast formation in cells cultured from EP$_4$ receptor knock-out mice. Yoshida et al in Proceedings of the National Academy of Sciences of the United States of America (2002) 99, 7, 4580-4585, by use of mice lacking each of the PGE$_2$ receptor EP subtypes, identified EP$_4$ as the receptor that mediates bone formation in response to PGE$_2$ administration. They also demonstrated a selective EP$_4$ receptor agonist (ONO-4819) consistently induces bone formation in wild type mice. Additionally, Terai et al in Bone 2005, 37(4), 555-562 have shown the presence of a selective EP$_4$ receptor agonist (ONO-4819) enhanced the bone-inducing capacity of rhBMP-2, a therapeutic cytokine that can induce bone formation.

Further research by Larsen et al in Acta. Physiol. Scand. (2005) 185, 133-140, shows the effects of PGE$_2$ on secretion in the second part of the human duodenum is mediated through the EP$_4$ receptor. Nitta et al in Scandinavian Journal of Immunology (2002), 56, 1, 66-75 has shown that a selective EP$_4$ receptor agonist ONO-AE 1-329 can protect against colitis in rats.

Dore et al in The European Journal of Neuroscience (2005) 22, 9, 2199-206, have shown that PGE$_2$ can protect neurons against amyloid beta peptide toxicity by acting on EP$_2$ and EP$_4$ receptors. Furthermore Dore has demonstrated in Brain Research (2005) 1066, (1-2), 71-77 that an EP$_4$ receptor agonist ONO-AE1-329 protects against neurotoxicity in an acute model of excitotoxicity in the brain.

Woodward et al in Journal of Lipid Mediators (1993), 6, (1-3), 545-53, found intraocular pressure could be lowered using selective prostanoid agonists. Two papers in Investigative Ophthalmology & Visual Science have shown the prostanoid EP$_4$ receptor is expressed in human lens epithelial cells (Mukhopadhyay et al 1999, 40(1), 105-12), and suggest a physiological role for the prostanoid EP$_4$ receptor in modulation of flow in the trabecular framework of the eye (Hoyng et al 1999, 40(11), 2622-6).

Compounds exhibiting EP$_4$ receptor binding activity and their uses as agonists have been described in, for example WO2009150118, WO2008136519, WO2008092860, WO2008092861, WO2008092862, WO2006137472, JP2006321737, WO2006052630, WO2006052893, WO2006016689

SUMMARY OF THE INVENTION

One of the objects of the present invention is the provision of compounds having an EP$_4$ receptor agonistic activity and specifically pharmaceutical compounds which are useful for the treatment or alleviation of Prostaglandin E mediated diseases.

The inventors of the present application have discovered novel compounds that are selective agonists of the EP$_4$ subtype of PGE$_2$ receptors. Specifically, the compounds according to the invention are provided with analgesic, antinflammatory, antiglaucoma activity, and also with antiosteoporosis and antiulcerative activity.

In accordance with a general aspect, the present invention provides cyclic amine compound of Formula (I):

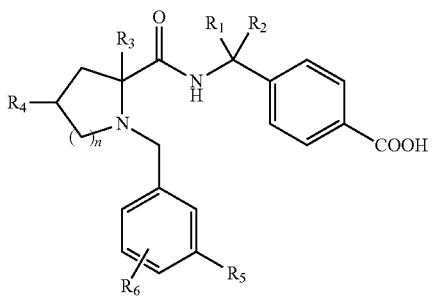

or a pharmaceutically acceptable salt thereof,
wherein:
R$_1$ and R$_2$ are independently hydrogen, linear o branched C$_{1-3}$ alkyl or joined together
they form a cyclopropyl ring;
n is 1 or 2,
R$_3$ is hydrogen or a linear or branched (C$_{1-3}$) alkyl,
R$_4$ is hydrogen, fluorine, or hydroxy group,
R$_5$ is halogen, cyano, linear o branched (C$_{1-3}$) alkyl, trifluoromethyl or trifluoromethoxy,
R$_6$ is hydrogen or halogen.

The term "halogen" as used herein refers to a fluorine, chlorine, bromine or iodine atom. In certain embodiments the halogen is fluorine.

The term "C$_{1-3}$ alkyl" as used herein refers to a linear or branched saturated hydrocarbon group containing of 1 to 3 carbon atoms. Examples of such groups include methyl, ethyl, n-propyl, isopropyl. In certain embodiments the C$_{1-3}$ alkyl is CH$_3$.

In this invention compounds of Formula (I) may exist as R and S enantiomers and as racemic mixture. This invention includes in its scope of protection all the possible isomers and racemic mixtures. Wherever should be present further symmetry centres, this invention includes all the possible diastereoisomers and relative mixtures as well.

In another aspect the invention concerns a compound of Formula (I) as medicament in particular it concerns its use for the treatment of pathologies where an agonist of the EP$_4$ receptor is needed, such as the treatment of pain, glaucoma, ulcerative colitis, osteoporosis.

DETAILED DESCRIPTION OF THE INVENTION

The invention thus concerns, in a general aspect, cyclic amine derivatives of Formula (I):

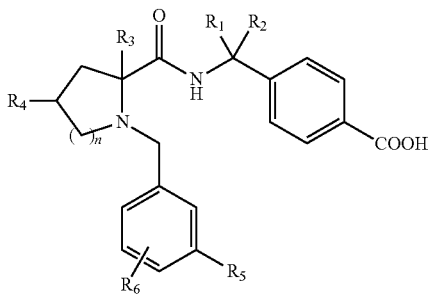

or a pharmaceutically acceptable salt thereof, wherein:
R$_1$ and R$_2$ are independently hydrogen, linear o branched C$_{1-3}$ alkyl or joined together
they form a cyclopropyl ring;
n is 1 or 2,
R$_3$ is hydrogen or a linear or branched C$_{1-3}$ alkyl,
R$_4$ is hydrogen, fluorine, or hydroxy group,
R$_5$ is halogen, cyano, linear o branched C$_{1-3}$ alkyl, trifluoromethyl or trifluoromethoxy,
R$_6$ is hydrogen or halogen.

In certain embodiments R$_6$ is in 4-position (para-position).

The term "halogen" as used herein refers to a fluorine, chlorine, bromine or iodine atom. In certain preferred embodiments the halogen is fluorine. In certain embodiments R$_6$ is fluorine. In certain embodiments both R$_5$ and R$_6$ are fluorine.

The term "C$_{1-3}$ alkyl" as used herein refers to a linear or branched saturated hydrocarbon group containing of 1 to 3 carbon atoms. Examples of such groups include methyl, ethyl, n-propyl, isopropyl.

In certain embodiments the C$_{1-3}$ alkyl is methyl.

In certain embodiments of the invention there is provided a subset (A) of compounds of formula (I) wherein n=1,
R$_1$ and R$_2$ are independently hydrogen, linear o branched C$_{1-3}$ alkyl or joined together
they form a cyclopropyl ring;
n is 1 or 2,
R$_3$ is hydrogen or a linear or branched C$_{1-3}$ alkyl,
R$_4$ is hydrogen, fluorine, or hydroxy group,
R$_5$ is halogen, cyano, linear o branched C$_{1-3}$ alkyl, trifluoromethyl or trifluoromethoxy,
R$_6$ is hydrogen or halogen.

In certain embodiments R$_6$ is in 4-position (para-position).

In the subset (A) of compounds of formula (I) the terms halogen and C$_{1-3}$ alkyl are as defined hereinabove.

In certain embodiments the halogen is fluorine.
In certain embodiments the substituent R$_6$ is halogen, preferably fluorine.
In certain embodiments the substituent R$_6$ is in the 4-position.
In certain embodiments the C$_{1-3}$ alkyl is methyl.
In certain embodiments R$_5$ is fluorine, trifluoromethyl or methyl.
In certain embodiments R$_6$ is hydrogen or fluorine.
In certain embodiments of the subset (A), R$_1$ is hydrogen; R$_2$ is methyl; R$_3$ is hydrogen; R$_4$ is hydrogen, fluorine or hydroxy; R$_5$ is fluorine, trifluoromethyl or methyl; R$_6$ is hydrogen.

In certain embodiments of the invention there is provided a subset (B) of compounds of formula (I) wherein n=2,
R$_1$ and R$_2$ are independently hydrogen, linear o branched C$_{1-3}$ alkyl or joined together
they form a cyclopropyl ring;
n is 1 or 2,
R$_3$ is hydrogen or a linear or branched C$_{1-3}$ alkyl,
R$_4$ is hydrogen, fluorine, or hydroxy group,
R$_5$ is halogen, cyano, linear o branched C$_{1-3}$ alkyl, trifluoromethyl or trifluoromethoxy,
R$_6$ is hydrogen or halogen.

The terms halogen and C$_{1-3}$ alkyl are as defined hereinabove.

In certain embodiments the substituent R$_6$ is halogen, preferably fluorine.
In certain embodiments the substituent R$_6$ may be in the 4-position.
In certain embodiments the halogen is fluorine.
In certain embodiments the C$_{1-3}$ alkyl is methyl.

In certain embodiments $R_5$ is fluorine, methyl, trifluoromethyl or trifluoromethoxy.

In certain embodiments $R_6$ is fluorine or hydrogen.

In certain embodiments both $R_5$ and $R_6$ are fluorine.

In certain embodiments $R_5$ is methyl and $R_6$ is hydrogen.

In certain embodiments of the subset (B) $R_1$ is hydrogen; $R_2$ is methyl; $R_3$ is hydrogen; $R_4$ is hydrogen; $R_5$ is fluorine, trifluoromethyl, methyl or trifluoromethoxy, $R_6$ is hydrogen.

In additional embodiments $R_1$ is hydrogen; $R_2$ is methyl; $R_3$ is hydrogen; $R_4$ is hydrogen; $R_5$ is fluorine, methyl, trifluoromethyl, or trifluoromethoxy; $R_6$ is hydrogen.

The term "pharmaceutically acceptable salts" as used herein, refers to salts prepared from pharmaceutically acceptable non-toxic bases or acids including inorganic or organic bases and inorganic or organic acids, quaternary ammonium salts and internally formed salts.

Salts derived from inorganic bases include aluminium, ammonium, calcium, copper, ferric, ferrous, lithium, magnesium, manganese salts, manganese, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethyl-aminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula (I) are meant to also include the pharmaceutically acceptable salts.

Furthermore, the compound of the formula (I) may form an acid addition salt or a salt with a base, depending on the kind of the substituents, and these salts are included in the present invention, as long as they are pharmaceutically acceptable salts.

The compounds (I) of the invention may be in crystalline forms. In certain embodiments, the crystalline forms of the compounds (I) are polymorphs.

The terms "the compound of the invention" and "the compounds of the present invention" refer to each of the compounds of formulae (I) and are meant to include their pharmaceutically acceptable salts, hydrates, solvates, and crystalline forms and also any suitable forms as illustrated hereinafter.

In certain embodiments, the compound of the Formula (I) may exist in the form of other tautomers or geometrical isomers in some cases, depending on the kinds of the substituents. In the present specification, the compound may be described in only one form of such isomers, but the present invention includes such isomers, isolated forms of the isomers, or a mixture thereof.

Furthermore, the compound of the Formula (I) may have asymmetric carbon atoms or axial asymmetries in some cases, and correspondingly, it may exist in the form of optical isomers such as an (R)-form, an (S)-form, and the like. The present invention includes both a mixture and an isolated form of these optical isomers.

Within the scope of the present invention are therefore included all stereoisomeric forms, including enantiomers, diastereoisomers, and mixtures thereof, including racemates and the general reference to the compounds of formulae (I) include all the stereoisomeric forms, unless otherwise indicated.

Additionally, the pharmaceutically acceptable prodrugs of the compound of the formula (I) are also included in the present invention. The pharmaceutically acceptable prodrug refers to a compound having a group which can be converted into an amino group, OH, COOH, or the like, by solvolysis or under a physiological condition. Examples of the groups for forming a prodrug include those as described in Prog. Med., 5, 2157-2161 (1985) or "Pharmaceutical Research and Development" (Hirokawa Publishing Company, 1990), vol. 7, Drug Design, 163-198.

Additionally, the present invention in certain embodiments also includes various hydrates or solvates, and polymorphism of the compound of the formula (I) and a pharmaceutically acceptable salt thereof. Furthermore, the present invention also includes the compounds labelled with various radioactive isotopes or non-radioactive isotopes.

Compounds according to the present invention include examples 1-20 as shown herein below, or a pharmaceutically acceptable salt thereof.

In certain embodiments, the present invention provides a compound selected from the group consisting of:

lithium 4-((1S)-1-(1-(3,4-difluorobenzyl)piperidine-2-carboxamido)ethyl)benzoate lithium 4-((1S)-1-(1-(3-methylbenzyl)piperidine-2-carboxamido)ethyl)benzoate lithium 4-((1S)-1-(1-(3-fluorobenzyl)piperidine-2-carboxamido)ethyl)benzoate lithium 4-((1S)-1-(1-(3-(trifluoromethyl)benzyl)piperidine-2-carboxamido)ethyl)benzoate lithium 4-((S)-1-((R)-1-(3-(trifluoromethyl)benzyl)piperidine-2-carboxamido)ethyl)benzoate lithium 4-((S)-1-((R)-1-(3-fluorobenzyl)piperidine-2-carboxamido)ethyl)benzoate lithium 4-((S)-1-((R)-1-(3-methylbenzyl)piperidine-2-carboxamido)ethyl)benzoate lithium 4-((S)-1-((R)-1-(3-(trifluoromethoxy)benzyl)piperidine-2-carboxamido)ethyl)benzoate lithium (R)-4-(1-(1-(3-(trifluoromethyl)benzyl)piperidine-2-carboxamido)cyclopropyl)benzoate lithium (R)-4-(1-(1-(3-methylbenzyl)piperidine-2-carboxamido)cyclopropyl)benzoate lithium (R)-4-(1-(1-(3-fluorobenzyl)piperidine-2-carboxamido)cyclopropyl)benzoate (R)-4-(1-(1-(4-fluoro-3-methylbenzyl)piperidine-2-carboxamido)cyclopropyl)benzoic acid lithium (R)-4-(1-(1-(4-fluoro-3-(trifluoromethyl)benzyl)piperidine-2-carboxamido) cyclopropyl)benzoate lithium 4-((S)-1-((R)-1-(3-fluorobenzyl)pyrrolidine-2-carboxamido)ethyl)benzoate lithium 4-((S)-1-((R)-1-(3-(trifluoromethyl)benzyl)pyrrolidine-2-carboxamido)ethyl)benzoate lithium 4-((S)-1-((R)-1-(3-methylbenzyl)pyrrolidine-2-carboxamido)ethyl)benzoate lithium 4-((S)-1-((R)-1-(3,4-difluorobenzyl)pyrrolidine-2-carboxamido)ethyl)benzoate lithium 4-((S)-1-((R)-2-methyl-1-(3-(trifluoromethyl)benzyl)pyrrolidine-2-carboxamido)ethyl)benzoate lithium 4-((S)-1-((2R,4R)-4-hydroxy-1-(3-(trifluoromethyl)benzyl)pyrrolidine-2-carboxamido)ethyl)benzoate lithium 4-((S)-1-((2R,4S)-4-fluoro-1-(3-(trifluoromethyl)benzyl)pyrrolidine-2-carboxamido)ethyl)benzoate lithium 4-((S)-1-((2R,4R)-4-hydroxy-1-(3-(trifluoromethyl)benzyl)pyrrolidine-2-carboxamido)ethyl)benzoate A further aspect of this invention concerns a process for the preparation of a compound of Formula (I) comprising the following steps represented in the general scheme below:

GENERAL SCHEME

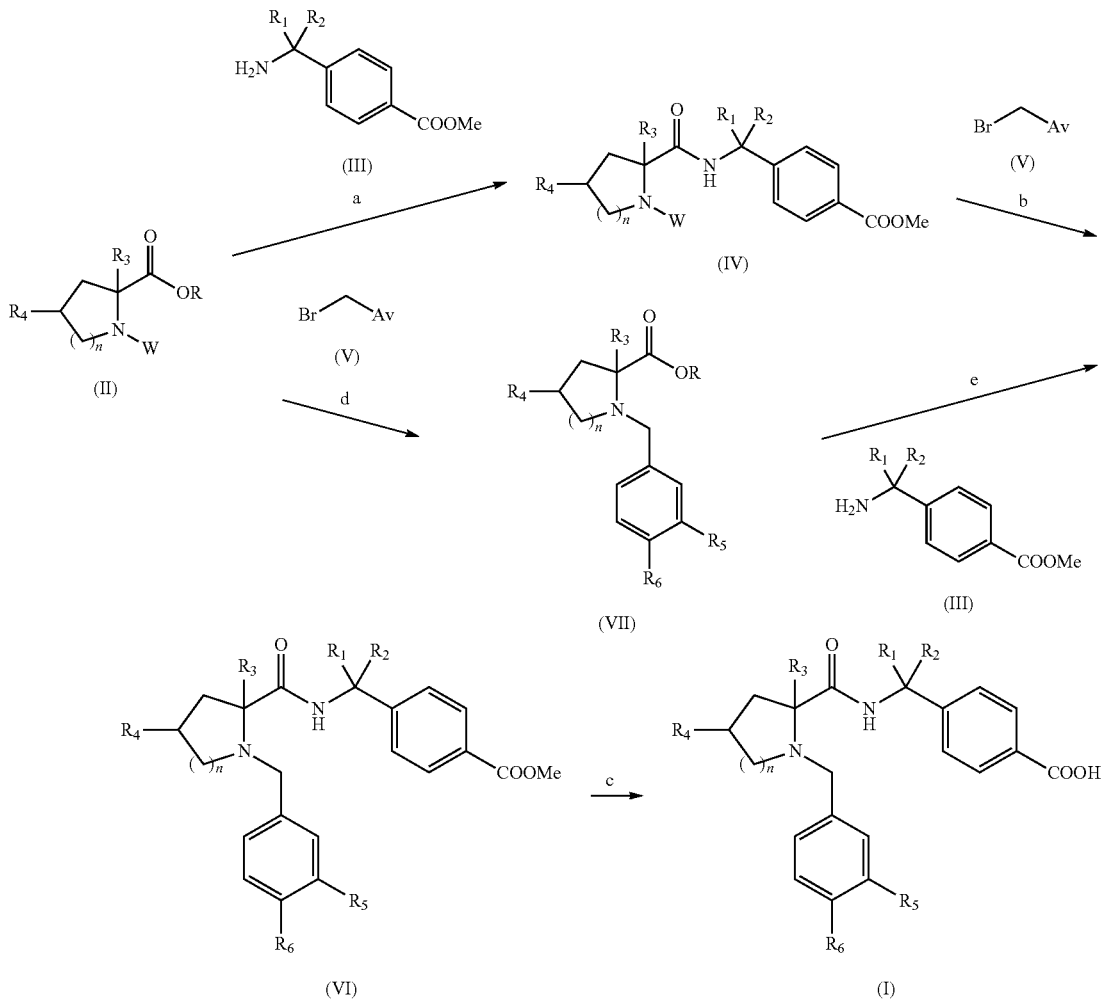

a) reacting a compound of formula (II) with a compound of formula (III) in the presence of a coupling reagent and of a base thus obtaining a compound of Formula (IV);
b) reacting a compound (IV) with compound of (V) in presence of a suitable base thus obtaining a compound of Formula (VI);
c) hydrolysing an ester compound (VI) with strong bases such as lithium hydroxide in a suitable solvent system such as 1,4-dioxane/H$_2$O, thus obtaining a compound of Formula (I);
d) reacting a compound (II) with a compound of (V) in presence of a suitable base thus obtaining a compound of Formula (VII);
e) reacting a compound of formula (VII) with a compound of formula (III) in the presence of a coupling reagent and in the presence of a base thus obtaining a compound of Formula (VI).

Preferred compounds of the invention are selected from the group consisting of:
lithium 4-((S)-1-((R)-1-(3-(trifluoromethyl)benzyl)piperidine-2-carboxamido)ethyl)benzoate
lithium (R)-4-(1-(1-(3-(trifluoromethyl)benzyl)piperidine-2-carboxamido)cyclopropyl)benzoate
(R)-4-(1-(1-(4-fluoro-3-methylbenzyl)piperidine-2-carboxamido)cyclopropyl)benzoic acid
lithium (R)-4-(1-(1-(4-fluoro-3-(trifluoromethyl)benzyl)piperidine-2-carboxamido)cyclopropyl)benzoate
lithium 4-((S)-1-((R)-1-(3-(trifluoromethyl)benzyl) pyrrolidine-2-carboxamido)ethyl)benzoate In the above general scheme, $R_1$, $R_2$, $R_3$, $R_4$, $R_5$, $R_6$ and n are as defined in formula (I), n is 1 or 2

R is selected from the group consisting of hydrogen, linear or branched $C_{1-3}$ alkyl and benzyl groups, W is selected from the group consisting of hydrogen, benzyl group and t-Butyl carbamate group.

It will be appreciated that compounds of formula (II), (IV) and (VII), may be converted into other compounds of formula (II), (IV) and (VII), by synthetic methods known to the skilled person in the art.

Examples of such conversion reactions are:

i) Compounds of formula (II) wherein R is $C_{1-3}$ alkyl, may be prepared by reacting corresponding compounds wherein R is hydrogen with alcohols, for example ethanol, in the presence of a suitable reactive reagent such as thionyl chloride.

ii) Compounds of formula (VII), when R is hydrogen, may be prepared by hydrolysis of the corresponding compounds of formula (VII), wherein R is $C_{1-3}$ alkyl. The hydrolysis is carried out in the presence of a base, for example lithium hydroxide in aqueous 1,4-dioxane.

iii) Compounds of formula (VII), when R is a substituted benzyl group, may be prepared by fluorination of corresponding compounds of formula (VII), wherein R is hydroxy group. The hydrolysis is carried out in the presence of diethylaminosulfur trifluoride at low temperature, typically −20° C.

Method of Synthesis

As above shown, according to a further aspect of this invention there is provided a process for the preparation of compound of formula (I).

In a more detailed way, the compounds of the present invention may be prepared according to the following schemes.

Unless otherwise indicated $R_1$, $R_2$, $R_3$, $R_4$, $R_5$, $R_6$ and n, in the reaction schemes and discussion that follow are as defined above, in formula (I).

The term "protecting group", as used hereinafter, means an amino protecting group which is selected from typical amino protecting groups as described in Protective Groups in Organic Synthesis edited by T. W. Greene et al. (John Wiley & Sons, 1999);

Compounds of formula (I) may be prepared by hydrolysis reaction of ester compounds of formula (VI) according to the reaction scheme 1.

SCHEME 1

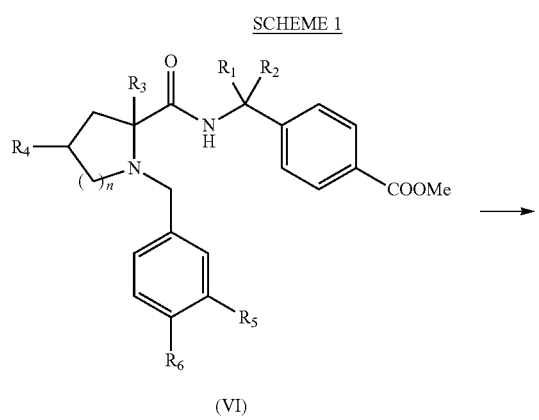

(VI)

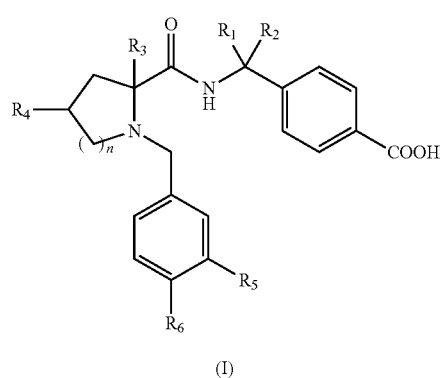

(I)

Hydrolysis can be carried out in presence of a base, for example lithium hydroxide in a suitable solvent such as in aqueous 1,4-dioxane.

In certain embodiments, this reaction may be carried out at room temperature.

Compounds of formula (VI) may be prepared according to reaction scheme 2.

SCHEME 2

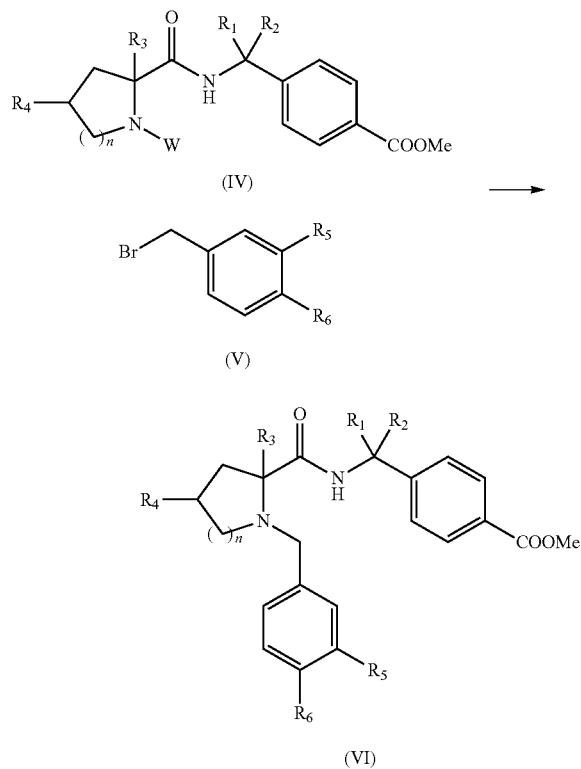

Compounds of formula (IV), wherein W is hydrogen, may be reacted with compounds of formula (V) in the presence of a suitable base, such as cesium carbonate, in a suitable solvent, for example acetonitrile. In certain embodiments the reaction is carried out at room temperature or in others under heating, for example at around 60° C.

Compounds of formula (IV), wherein W is hydrogen, may be prepared from corresponding compounds of formula (IV) wherein W is benzyl group or t-butyl carbamate group.

In certain embodiments wherein W is t-butyl carbamate, the deprotection step can be carried out in presence of trifluoroacetic acid in a suitable solvent such as dichloromethane.

In other embodiments wherein W is a benzyl group, the deprotection step can be carried out by hydrogenolysis typically in a suitable solvent such as ethanol.

Compounds of formula (IV) may be prepared according to reaction scheme 3.

SCHEME 3

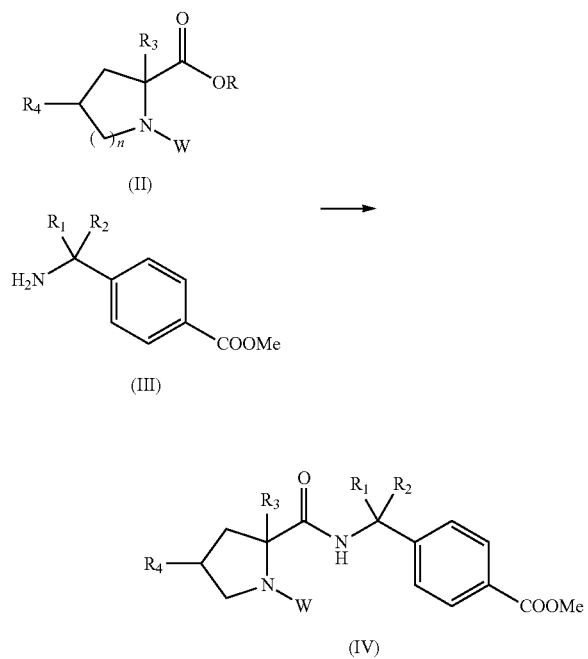

In certain embodiments, the compounds of formula (II), wherein R is hydrogen and W is a benzyl group or t-butyl carbamate, are reacted with compounds of formula (III) in the presence of a suitable coupling reagent, for example selected from (2-(6-Chloro-1H-benzotriazole-1-yl)-1,1,3,3-tetramethylaminium hexafluorophosphate) (HCTU), O-(7-Azabenzotriazol-1-yl)-N,N,N',N'-tetramethyluronium hexafluorophosphate (HATU), (1-Ethyl-3-(3-dimethyllaminopropyl) carbodiimide hydrochloride) and 1-Hydroxybenzotriazole and mixtures thereof. Typically, the reaction is carried out in an aprotic solvent, for example a halohydrocarbon, such as dichloromethane, N,N-dimethylformamide, or acetonitrile or mixture thereof, typically at room temperature, in presence of a suitable base, such as N,N-diisopropylamine.

Compounds of formula (III) are known, for example from the International Patent applications WO 2005105733 and WO2008104055.

Alternatively compound of formula (VI) may be prepared according to reaction scheme 4.

SCHEME 4

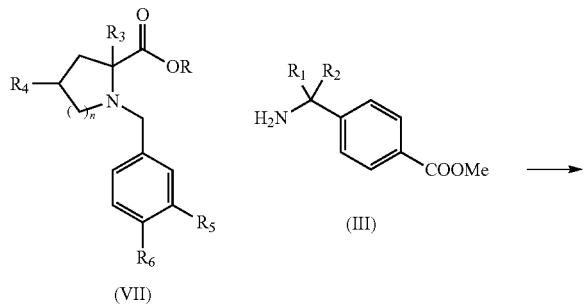

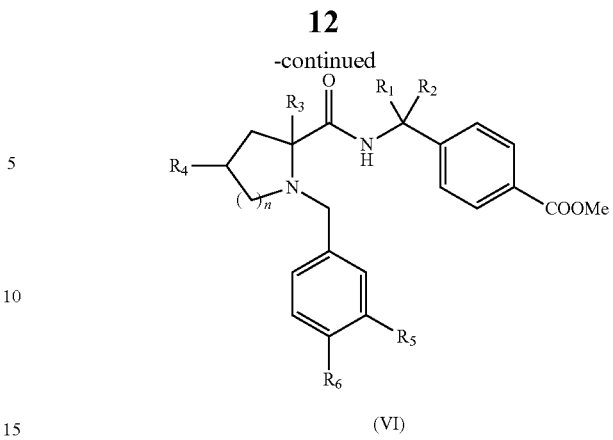

In certain embodiments, the compounds of formula (VII), wherein R is hydrogen, are reacted with compounds of formula (III) in the presence of a suitable coupling reagent, for example selected from (2-(6-Chloro-1H-benzotriazole-1-yl)-1,1,3,3-tetramethylaminium hexafluorophosphate) (HCTU), O-(7-Azabenzotriazol-1-yl)-N,N,N',N'-tetramethyluronium hexafluorophosphate (HATU), (1-Ethyl-3-(3-dimethyllaminopropyl)carbodiimide hydrochloride) and 1-Hydroxybenzotriazole or mixtures thereof.

In certain embodiments the reaction is carried out in an aprotic solvent, for example a halohydrocarbon, such as dichloromethane, N,N-dimethylformamide, or acetonitrile or mixtures thereof, typically at room temperature, in presence of a suitable base.

In certain embodiments, the compounds of formula (VII), wherein R is hydrogen, may be prepared by hydrolysis of the corresponding compounds of formula (VII), wherein R is $C_{1-3}$ alkyl. In certain embodiments, the hydrolysis is carried out in the presence of a base for example lithium hydroxide, typically in suitable solvent such as aqueous 1,4-dioxane.

In certain embodiments, the compounds of formula (VII) may be prepared according to reaction scheme 5.

SCHEME 5

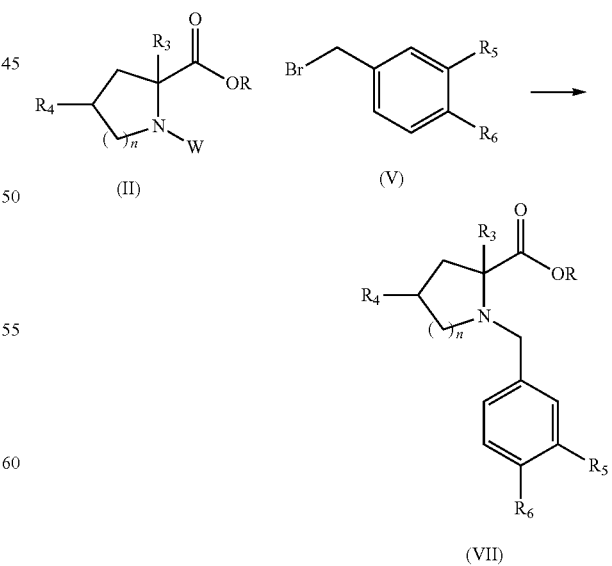

In certain embodiments, the compounds of formula (II), wherein R is $C_{1-3}$ alkyl or hydrogen and W is hydrogen, may be reacted with compounds of formula (V) in the presence of a suitable base for example cesium carbonate, in a suitable solvent such as acetonitrile. In certain embodiments the reaction is carried out at room temperature, in other embodiments the reaction is carried out under heating, for example at around 60° C.

In accordance with certain embodiments, the compounds of formula (II) wherein W and $R_4$ are hydrogen, n is 1 and $R_3$ is methyl, may be prepared according synthetic route described in scheme 6.

SCHEME 6

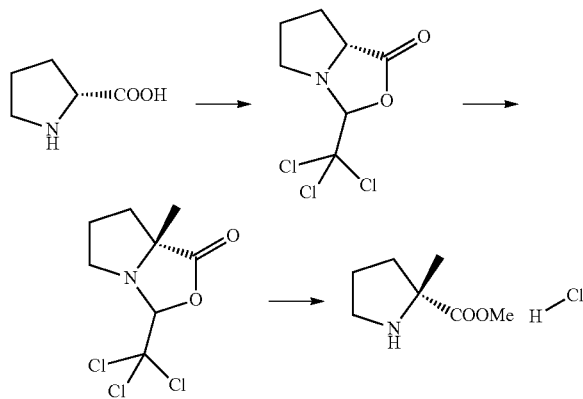

According to certain embodiments of the invention, the compounds (I) are obtained using a simple process, easy to scale-up and avoiding lengthy and expensive preparation steps, obtaining high yield of a stable pharmaceutical grade compound of formula (I).

Typically, the various methods described above may be useful for the introduction of the desired group at any stage in the stepwise formation of the required compound, and it will appreciated that these general methods can be combined in different way in such multi-stage processes. Typically, the sequence of the reactions in multi-stage processes are chosen so that the reaction conditions used do not affect groups in the molecule which are in the final product.

In certain embodiments where an enantiomer of a compound of the general formula (I) is required, this may be obtained by resolution of a corresponding enantiomeric mixture of such compound of formula (I) by using conventional methods such as by chiral HPLC procedure.

In certain embodiments the compounds of general formula (I) are in the form of salts, specifically pharmaceutically acceptable salts. These salts may be obtained using conventional methods, for example by reacting the compound having general formula (I) in the form of a free base with a suitable acid in a suitable solvent for example an alcohol, such as ethanol or an ether such as diethyl ether or an ester such as ethyl acetate.

In certain embodiments the compounds of general formula (I) may be isolated in association with solvent molecules for example by evaporation or crystallisation from a suitable solvent to provide the corresponding solvates.

The Inventors have found that the general family of the compounds of formula (I) have affinity for and are specific agonists of $PGE_2$ receptors, in particular of $EP_4$ subtype of $PGE_2$ receptors.

The compounds of general formula (I) are useful in the treatment of Prostaglandin E mediated conditions or diseases.

Thus, according to an additional aspect the invention concerns compounds of Formula (I) for use as a medicament the treatment of pathologies or disorders where an agonist of the $EP_4$ receptor is needed.

The compounds of formula (I) are $EP_4$ receptor agonists and may therefore be useful in treating $EP_4$ receptor mediated diseases.

More particularly, the compounds of the present invention are believed to be of potential use in the treatment or prophylaxis of diseases or disorders where an $EP_4$ receptor agonist is required such as pain, for example, chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds may be particularly useful in the treatment of neuropathic pain and symptoms associated therewith. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD; gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease, diarrhea, constipation); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds may also be useful in the treatment of immunological diseases such as autoimmune diseases, immunological deficiency diseases or organ transplantation.

The compounds may also be effective in increasing the latency of HIV infection.

The compounds may also be useful in the treatment of diseases of excessive or unwanted platelet activation such as intermittent claudication, unstable angina, stroke, and acute coronary syndrome (e.g. occlusive vascular diseases).

The compounds may also be useful as a drug with diuretic action, or may be useful to treat overactive bladder syndrome.

The compounds may also be useful in the treatment of impotence or erectile dysfunction.

The compounds of formula (I) may also be useful in the treatment of various Bone Disorders as herein below defined, which includes the treatment of bone fractures, bone injury or bone defects. For example, the compounds of the invention may be useful in enhancement of bone formation i.e. osteogenesis, such as increasing bone mass, bone volume, osteoblast number or osteoblast survival.

The compounds of formula (I) may therefore be useful in the treatment of bone disease, including genetic disorders, that are characterised by abnormal bone metabolism or resorption such as osteoporosis (especially postmenopausal osteoporosis, glucocorticoid induced osteoporosis, hyperthyroidism-induced osteoporosis, immobilisation-induced osteoporosis, heparin-induced osteoporosis and immunosuppressive-induced osteoporosis as well as long term complications of osteoporosis such as curvature of the spine, loss of height and prosthetic surgery), abnormally increased bone turnover, hyper-calcemia (including humoral hypercalcemia), hyperparathyroidism, Paget's bone diseases, osteolysis (including periprosthetic osteolysis), hypercalcemia of malignancy with or without bone metastases, hypercalcemia of fracture healing, rheumatoid arthritis, osteoarthritis (including disease modifying in osteoarthristis such as cartilage/bone repair), ostealgia, osteopenia, calculosis, lithiasis (especially urolithiasis), gout and ankylosing spondylitis, tendonitis, bursitis, malignant bone tumour e.g. osteosarcoma, osteogenesis imperfecta, metastatic bone disease, alveolar bone loss, post-osteomy and childhood idiopathic bone loss.

The compounds of formula (I) may also be useful in bone remodelling and/or promoting bone generation and/or promoting fracture healing. For example, the compounds of the present invention may be useful in fracture healing e.g. long bone fractures and fractures of other bones. The compounds of the present invention may also be useful in healing fractures of the head, face and neck caused e.g. by injury. The compounds of the present invention may also be useful in bone grafting including replacing bone graft surgery entirely, enhancing the rate of successful bone grafts, bone healing following facial reconstruction, maxillary reconstruction, mandibular reconstruction, craniofacial reconstruction e.g. of craniofacial defects such as orofacial defects at birth (including orofacial clefts such as cleft palate), prosthetic ingrowth, vertebral synostosis, long bone extension, spinal fusion, and sternotomy. The compounds of the invention may also be useful in treating bone defects that might evolve around defects that occur during war.

The compounds of the invention may also be useful in periodontal indications such as periodontal disease (periodontitis), tooth loss, and peridontal augmentation e.g. in preparation for tooth implants.

The compounds of the present invention may also be useful in facilitating joint fusion, facilitating tendon and ligament repair, reducing the occurrence of secondary fracture, treating avascular necrosis, facilitating cartilage repair, facilitating bone healing after limb transplantation and repairing damage caused by metastatic bone disease.

The compounds may also be useful for attenuating the hemodynamic side effects of NSAIDs and COX-2 inhibitors.

The compounds may also be useful in the treatment of cardiovascular diseases such as hypertension or myocardial ischemia; functional or organic venous insufficiency; varicose therapy; haemorrhoids; and shock states associated with a marked drop in arterial pressure (e.g. septic shock).

The compounds may also be useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds may also be useful in the treatment of neurological disorders and may be useful as neuroprotecting agents. The compounds may also be useful in the treatment of neurodegeneration following stroke, cardiac arrest, pulmonary bypass, traumatic brain injury, spinal cord injury or the like.

The compounds may also be useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds may also be useful in the treatment of kidney dysfunction (nephritis, particularly mesangial proliferative glomerulonephritis, nephritic syndrome), liver dysfunction (hepatitis, cirrhosis) and gastrointestinal dysfunction (diarrhoea).

It is to be understood that as used herein any reference to treatment includes both treatment of established symptoms and prophylactic treatment.

It is to be understood that reference to treatment includes both treatment of established symptoms and prophylactic treatment, unless explicitly stated otherwise. In a further aspect, the present invention concerns a compound of Formula (I), for use as a medicament.

In another aspect the invention provides a pharmaceutical composition comprising a compound of Formula (I) and a pharmaceutically acceptable carrier.

The compound of Formula (I) may be used in combination with a pharmaceutically acceptable carrier and, optionally, with suitable excipients, to obtain pharmaceutical compositions.

The term "pharmaceutically acceptable carrier" means solvents, carrier agents, diluting agents and the like which are used in the administration of compounds of the invention.

In certain embodiments, the pharmaceutical compositions of the invention may be in solid or liquid form.

The pharmaceutical compositions in solid form may contain suitable excipients such as fillers, lubricants, binding agents, wetting agents, disintegrants, colorants and flavouring agents and mixtures thereof. For example the tablets may contain pre-gelatinised starch, microcrystalline cellulose, sodium glycolate starch, talc, lactose, magnesium stearate, sucrose, stearic acid, mannitol.

The pharmaceutical compositions in liquid form, typically may be provided as solutions, suspensions, emulsion, syrups, elixir. Typically, the compositions in liquid form may contain suspending agents, emulsifying agents, carriers, preservatives and colorants, flavouring agents.

Typically, the pharmaceutical compositions of the invention can be administered by parenteral, oral, buccal, sublingual, nasal, rectal, topical or transdermal administration. Pharmaceutical compositions for oral administration are generally preferred.

The pharmaceutical compositions of the invention suitable for the oral administration typically, will be discrete units in solid form such as in the form of tablets, capsules, cachets, powders, granules, lozenges, patches, suppositories, pellets, or in liquid form such as liquid preparations, injectable or infusible solutions or suspensions.

The pharmaceutical compositions for parenteral administration typically include sterile preparations in the forms of solutions or suspensions. In certain embodiments the compositions for parenteral administration are aqueous based solution suitable for injection or infusion. In certain embodiments such compositions for parenteral administration includes one or more adjuvants such as buffering agents, preservatives, antibacterial agents, surfactants and mixtures thereof.

The pharmaceutical compositions for topical administration may be formulated as creams, pastes, oils, ointments, emulsions, foams, gels, drops, spray solutions and transdermal patches.

In certain embodiments the pharmaceutical composition of the invention includes 0.1 to 99% by weight of the compound of formula (I) as active ingredient. In certain embodiments the amount of the compound of formula (I) is 1 to 30% by weight. The dosage of the compound of formula (I) to be administered depends on the severity of the disease, the weight, the age and general conditions of the patient in need of treatment.

For example a suitable unit dosage may vary of from 0.01 to 1000 mg or typically of 1.0 to 300 mg to be administered one or more in a day, for example twice a day usually at regular intervals. The duration of the therapy depends on the severity of the illness and general condition of the patients and may be varied by the physician an extended for certain weeks or months.

According to another aspect, the use of a compounds of the general formula (I) for the manufacture of a medicament for the treatment of pathologies or diseases which require the administration of an agonist of the $EP_4$ receptor, such as the treatment of inflammatory pain, osteoarthritis, arthritis.

In accordance to certain embodiments, the present invention provides for a pharmaceutical composition comprising a compound of formula (I) in association with an additional active ingredient and a pharmaceutically acceptable excipient.

Said additional active ingredients may be an additional compound of formula (I) or a different chemical entity having similar or different activity.

In certain embodiments said additional active ingredients is selected from the antinflammatory compounds, such as FANS or cortisonic compounds.

The invention will be now detailed by means of the following examples relating to the preparation of some embodiments of the compounds of the invention and to the evaluation of their activity against $EP_4$ receptor.

The following Descriptions relating to intermediate products and Examples illustrating the preparation of certain compounds of formula (I) or salts thereof follow below. The descriptions illustrate the preparation of intermediates used to make compounds of formula (I) or salts thereof.

In the procedures that follow, after each starting material, reference to a description is provided. This is provided merely for assistance to the skilled chemist. The starting material may not necessarily have been prepared from the Description referred to. The stereochemistry of Descriptions and Examples has been assigned on the assumption that the absolute configuration centres are retained.

The yields are calculated assuming that products were 100% pure if not stated otherwise.

Compound are named using ChemBioDraw Ultra 12.0 (CambridgeSoft Corp., 100 CambridgePark Drive, Cambridge, Mass. 02140)

Reagents used in the following examples were commercially available from various suppliers (for example Sigma-Aldrich, Acros, Matrix scientific, Manchester or Apollo) and used without further purifications.

Reactions in anhydrous environment were run under a positive pressure of dry N2 and solvents were used in dry form.

For reaction involving microwave irradiation, an Initiator 2.5 System was used.

Purification was performed using Biotage automatic flash chromatography systems (Sp1 and Isolera systems), Companion CombiFlash (ISCO) automatic flash chromatography, Flash Master or Vac Master systems.

Flash chromatography was carried out on silica gel 230-400 mesh (supplied by Merck AG Darmstadt, Germany), Varian Mega Be—Si pre-packed cartridges, pre-packed Biotage silica cartridges (e.g. Biotage SNAP-Si cartridges), Waters PoraPak RXN RP cartridges, Biotage SNAP-C18.

SPE-Si cartridges are silica solid phase extraction columns.

PoraPakRXN RP cartridges are polimer based reverse phase resin.

Biotage SNAP C18 Gold cartridges are silica based reverse phase column. SPE-SCX cartridges are ion exchange solid phase extraction columns supplied by Varian. The eluent used with SPE-SCX cartridges is dichloromethane and methanol or only methanol followed by 2N ammonia solution in methanol. The collected fractions are those eluted with ammonia solution in methanol.

Thin layer chromatography was carried out using Merck TLC plates Kieselgel 60F-254, visualized with UV light, aqueous permanganate solution, iodine vapours.

Proton Nuclear Magnetic Resonance (1H NMR) spectra were recorded on Bruker Avance 400 MHz instrument and on Bruker Avance III plus 400 MHz. TMS was used as internal standard. Chemical shifts are reported in ppm (δ) using the residual solvent line as internal standard. Splitting patterns are designated as: s, singlet; d, doublet; t, triplet; q, quartet; m, multiplet; b, broad signal. The NMR spectra were recorded at temperature ranging from 25° C. to 90° C. When more than one conformer was detected the chemical shifts of the most abundant one is usually reported.

In the analytical characterisation of the described compounds "MS" refers to Mass Spectra taken by Direct infusion Mass or to a mass Spectra associated with peaks taken by UPLC/MS or HPLC/MS analysis, where the Mass Spectrometer used is as mentioned below.

Direct infusion Mass Spectra (MS) were run on a Ion Trap Thermo LCQ classic spectrometer, operating in positive ES (+) and negative ES (−) ionization mode using different columns and operating procedures listed below:

Phenomenex Gemini-NX C18 column (100×2 mm, 3 μm particle size), column T=35° C. Mobile phase: A (water+0.1% formic acid)/B (acetonitrile+0.1% formic acid), Gradient: 10% B at t=0 min up to 90% B at t=12 min using different gradient curves, flow rate: 0.3 ml/min;

Acquity™ UPLC-BEH C18 column (50×21 mm, 1.7 μM particle size), column T=35° C. Mobile phase: A (water+0.1% formic acid)/B (acetonitrile+0.1% formic acid), Gradient: 5% B at t=0 min up to 100% B at t=4.5 min, using different gradient curves, flow rate: 0.5 ml/min;

Zorbax SB C18 column (2.1×50 mm, 3.5 μm particle size) column T=35° C. Mobile phase: A (water+0.1% formic acid)/B (acetonitrile+0.1% formic acid), Gradient: 10% B at t=0 min up to 90% B at t=12 min using different gradient curves, flow rate: 0.4 ml/min.

HPLC spectra were performed on a Waters Alliance 2965 instrument equipped with a Waters 2996 UV-Vis detector using a Phenomenex Luna C18 column (150×4.6 mm, 5 μm particle size). [Mobile phase: different mixtures of acetonitrile/methanol/KH2PO4 (20 mM pH 2.5); Elution time: 35 min; column T=30° C.; flow rate=0.6 ml/min. UV detection wavelength range from 220 up to 300 nm]

Total ion current (TIC) and DAD UV chromatografic traces together with MS and UV spectra were taken on a UPLC/MS Acquity™ system equipped with 2996 PDA detector and coupled to a Waters Micromass ZQ™ Mass Spectrometer operating in positive or negative electrospray ionisation mode. UPLC analysis were performed using an Acquity™ UPLC-BEH C18 column (50×21 mm, 1.7 μM particle size), column T=35° C. Mobile phase: A (water+0.1% formic acid)/B (acetonitrile+0.1% formic acid), Gradient: 5% B at t=0 min, up to 100% B at t=2 min or 4.5 min using different gradient curves, flow rate: 0.5 ml/min.

LCMS were taken on a quadrupole Mass spectrometer on Agilent LC/MSD 1200 Series using Column: Welchrom XB-C18 (50×4.6 mm, 5 μm) operating in ES (+) or (−) ionization mode at T=30° C. and with a flow rate=1.5 ml/min.

HPLC spectra for chiral purity determinations were performed on Agilent 1200 instrument and UV detector DAD G1315D using a Daicel Chiralpack IC column (250×4.6 mm, 5 μm particle size) or a Daicel Chiralpack AD-H column (250×4.6 mm, 5 μm particle size). [Mobile phases: isocratic mixtures A (70% n-heptane 30% ethanol+0.1% trifluoroacetic acid) or B (80% n-hexane 20% isopropanol+0.2% trifluoroacetic acid), up to 60 min of elution at 30° C., flow rate of 0.5 ml/min].

Purifications by means of preparative chiral HPLC were performed on Shimadzu Preparative Liquid Chromatograph LC-8A apparatus and UV detector SPD-20A using a Daicel Chiralpack IC column (2×25 cm, 5 μm particle size) or a Daicel Chiralpack AD-H column (2×25 cm, 5 μm particle size).

[Mobile phases: isocratic premixed mixtures A (70% n-heptane 30% ethanol+0.1% trifluoroacetic acid) or B (80% n-hexane 20% isopropanol+0.2% trifluoroacetic acid).

Specific Mobile phase and operating conditions will be specified each time.

ABBREVIATIONS

BAIB—bis(acetoxy)iodobenzene
BF$_3$.OEt$_2$—Boron trifluoride diethyl etherate
Boc$_2$O—Di-tert-butyl dicarbonate
cHex—Cyclohexane
s-BuLi—sec-Butyllithium
t-Buli—tert-Butyllithium
DAST—Diethylaminosulfur trifluoride
1,2 DCE—1,2-Dichloroethane
DCM—dichloromethane
DEA—diethylamine
DMAP—4-Dimethylaminopyridine
DMF—Dimethylformamide
DIPEA—N,N-Diisopropylethylamine
EDC HCl—1-ethyl-3-(3-dimethylaminopropyl)carbodiimide)
EtOAc—Diethylacetate
Et$_2$O—Diethylether
Et$_3$SiH—Triethylsilane
HATU—O-(7-azabenzotriazol-1-yl)-N,N,N',N'-tetramethyluronium hexafluorophosphate
HBTU—O-Benzotriazole-N,N,N',N'-tetramethyl-uronium-hexafluorophosphate
HCTU—(2-(6-Chloro-1H-benzotriazole-1-yl)-1,1,3,3-tetramethylaminium hexafluorophosphate)
HOBT—N-Hydroxybenzotriazole
IPA—2-propanol
LDA—Lithium diisopropylamide
LiEt$_3$BH—Lithium triethylborohydride
LiHMDS—Lithium bis(trimethylsilyl)amide
MeCN—Acetonitrile
MTBE—Methyl tert-butyl ether
NaBH(OAc)$_3$—Sodium triacetoxyborohydride
NaBH$_4$—Sodium borohydride
PTSA—p-Toluene sulfonic acid
Py—Pyridine
RT—Room Temperature
TBAF—Tetra-n-butylammonium fluoride
TBDMSCl—tert-Butyldimethylsilyl chloride
TBDPSCl—tert-butyldiphenylsilyl chloride
TEA—Triethylamine
TEMPO—2,2,6,6-Tetramethylpiperidinyloxy
TFA—Trifluoroacetic acid
TFAA—Trifluoroacetic anhydride
TMEDA—Tetramethylethylenediamine
TMSCHN2— Trimethylsilyldiazomethane
p-TSA—p-Toluenesulfonic acid
THF—Tetrahydrofuran

DESCRIPTIONS

Description 1: (7aR)-3-(trichloromethyl)tetrahydropyrrolo[1,2-c]oxazol-1(3H)-one (D1)

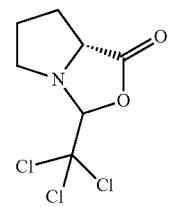

To a solution of D-proline (0.4 g, 3.48 mmol) in MeCN (8 ml) the trifluoroacetaldehyde (0.68 ml, 6.94 mmol) was added and the resulting mixture was stirred at RT for 8 hrs. Solvents were evaporated and the residue was triturated with diethyl ether. After solvent filtration and drying, 0.23 g of title compound (D1) was isolated.

MS: (ES/+) m/z: 244.0 [MH$^+$] C7H8Cl3NO2 requires 242.96

$^1$H NMR (400 MHz, CHCl3-d) δ (ppm): 4.15 (dd, J=4.5, 8.6 Hz, 1H), 3.52-3.36 (m, J=7.0, 7.0, 10.5 Hz, 1H), 3.22-3.07

(m, 1H), 2.33-2.20 (m, 1H), 2.19-2.08 (m, 1H), 1.96 (quind, J=5.9, 12.1 Hz, 1H), 1.84-1.69 (m, 1H), 1.61 (br. s., 1H).

Description 2: (7aR)-7a-methyl-3-(trichloromethyl)tetrahydropyrrolo[1,2-c]oxazol-1(3H)-one (D2)

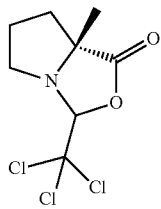

To a solution of (7aR)-3-(trichloromethyl)tetrahydropyrrolo[1,2-c]oxazol-1(3H)-one (D1) (0.2 g, 0.82 mol) in THF (10 ml) cooled at −78° C. LDA 2M sol in THF/heptane (0.58 ml, 1.17 mol) was added and the mixture stirred 30 min. Diiodomethane (0.185 ml, 2.97 mol) was added and the temperature was allowed to warm to −40° C. over a period of 2 hrs then left at this temperature for an additional hour. The resulting mixture was partitioned between DCM and H₂O. The aqueous phase was extracted with DCM (2×10 ml); the organic phases were collected, dried over Na₂SO₄ and evaporated in vacuo. The residue was purified by SPE-Si cartridge (25 g) eluting with DCM. Collected fractions after solvent evaporation afforded title compound (D2) in mixture (4:1) with starting material (110 mg).

MS: (ES/+) m/z: 258.0 [MH⁺] C8H10Cl3NO2 requires 256.98

Description 3: (R)-methyl 2-methylpyrrolidine-2-carboxylate hydrochloride (D3)

To a solution of (7aR)-7a-methyl-3-(trichloromethyl)tetrahydropyrrolo[1,2-c]oxazol-1(3H)-one (D2) (0.11 g, 0.42 mol) in dry MeOH (2 ml), HCl 1M sol in MeOH (0.3 ml, 0.85 mol) was added and the mixture refluxed under a constant current of nitrogen for 1 h. Solvent was evaporated to afford the title compound (D3) 60 mg.

MS: (ES/+) m/z: 144.1 [MH⁺] C7H13NO2 requires 143.09 (as free base).

General Procedure for Amides Preparation

Selected acid (1 eq), HOBT.H₂O (1 eq) and EDC.HCl (1.5 eq) were suspended in DCM and the resulting mixture was stirred 1 h at RT. A solution of a selected amine (1 eq) and TEA (1 eq) in DCM was added and the mixture was stirred at RT for 1/48 hrs. Solvents were evaporated in vacuo and the resulting residue was re-dissolved in DCM. The mixture was then added to a saturated aqueous solution of NaHCO₃ and extracted with dichloromethane. The organic phase was dried over Na₂SO₄ and the solvent was removed under reduced pressure. The crude material was purified on SPE-Si cartridge or SNAP-Si column eluting with a mixture of DCM/MeOH 98:2 or DCM/EtOAc from 100:0 to 70:30 affording the title amide compound.

Description 4: tert-butyl 2-(((S)-1-(4-(methoxycarbonyl)phenyl)ethyl)carbamoyl)piperidine-1-carboxylate (diastereoisomers mixture) (D4)

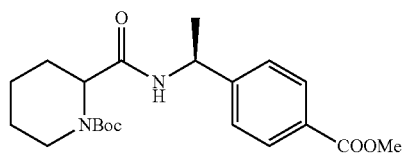 [SMILES: COC(=O)c1ccc([C@H](C)NC(=O)C2CCCCN2C(=O)OC(C)(C)C)cc1]

The title compound (D4) (1.95 g) was prepared according to the general procedure for amides preparation starting from 1-(tert-butoxycarbonyl)piperidine-2-carboxylic acid (1.17 g, available from Sigma Aldrich #495875), and (S)-methyl 4-(1-aminoethyl)benzoate hydrochloride (1.1 g, for preparation see published International Patent application WO 2005/105733). Reaction time: 18 hrs.

MS: (ES/+) m/z: 391.3 [MH⁺] C21H30N2O5 requires 390.22

Chiral HPLC [Phenomenex Lux Cellulose-1; Mobile phase A: 90% n-hexane (+0.1% DEA), B: 10% IPA; DAD: 237 nm]: Peak 1 retention time: 11.6 min; peak 2 retention time: 16.16 min.

¹H NMR (400 MHz, CHCl3-d) δ (ppm): 8.01 (d, 4H) 7.36 (t, 4H) 6.12-6.82 (m, 2H) 5.17 (br. s., 2H) 4.74 (br. s., 2H) 3.81-4.25 (m, 8H) 2.81 (br. s., 1H) 2.66 (t, 1H) 2.28 (br. s., 2H) 1.42-1.75 (m, 4H).

Description 5: (R)-tert-butyl 2-(((S)-1-(4-(methoxycarbonyl)phenyl)ethyl)carbamoyl)piperidine-1-carboxylate (D5)

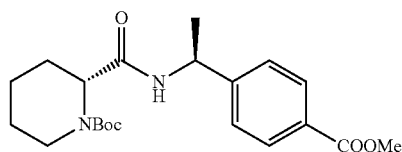

The title compound (D5) (405 mg) was prepared according to the general procedure for amides preparation starting from (R)-1-(tert-butoxycarbonyl)piperidine-2-carboxylic acid (250 mg, available from Sigma Aldrich #516341), and (S)-methyl 4-(1-aminoethyl)benzoate hydrochloride (235 mg). Reaction time: 18 hrs.

MS: (ES/+) m/z: 391.3 [MH⁺] C21H30N2O5 requires 390.22

Chiral HPLC [Phenomenex Lux Cellulose-1; Mobile phase A: 90% n-hexane (+0.1% DEA), B: 10% EtOH; DAD: 237 nm]: Peak retention time: 9.6 min.

¹H NMR (400 MHz, CHCl3-d) δ (ppm): 8.02 (d, J=8.3 Hz, 2H), 7.36 (d, J=7.8 Hz, 2H), 6.75-6.40 (m, 1H), 5.23-5.11 (m, 1H), 4.81-4.70 (m, 1H), 4.10-3.95 (m, 1H), 3.93 (s, 3H), 2.72-2.60 (m, 1H), 2.36-2.20 (m, 1H), 1.67-1.61 (m, 1H), 1.58-1.47 (m, 15H), 1.46-1.36 (m, 1H).

Description 6: (R)-cert-butyl 2-((1-(4-(methoxycarbonyl)phenyl)cyclopropyl)carbamoyl)piperidine-1-carboxylate (D6)

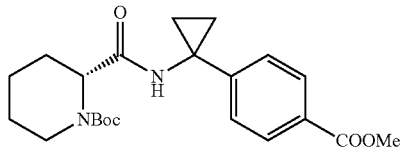

The title compound (D6) (650 mg) was prepared according to the general procedure for amides preparation starting from (R)-1-(tert-butoxycarbonyl)piperidine-2-carboxylic acid (500 mg, available from Sigma Aldrich #516341), and methyl 4-(1-aminocyclopropyl)benzoate hydrochloride (470 mg). Reaction time: 18 hrs.

MS: (ES/+) m/z: 403 [MH$^+$] C22H30N2O5 requires 402.22

Chiral HPLC [DAICEL OD-H; Mobile phase A: 80% n-hexane (+0.1% DEA), B: 20% IPA; DAD: 248 nm]: Peak retention time: 13.04 min.

$^1$H NMR (400 MHz, CHCl3-d) δ (ppm): 7.96 (d, J=8.1 Hz, 2H), 7.24 (d, J=8.1 Hz, 2H), 7.02-6.74 (m, 1H), 4.81-4.68 (m, 1H), 4.19-4.00 (m, 1H), 3.92 (s, 3H), 2.88-2.69 (m, 1H), 2.39-2.17 (m, 1H), 1.66 (br. s., 3H), 1.52 (s, 9H), 1.34 (d, J=18.6 Hz, 6H).

Description 7: (R)-tert-butyl 2-(((S)-1-(4-(methoxycarbonyl)phenyl)ethyl)carbamoyl)pyrrolidine-1-carboxylate (D7)

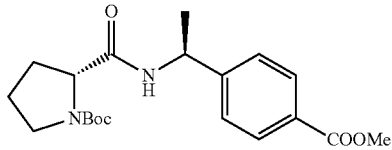 [SMILES: COC(=O)c1ccc([C@H](C)NC(=O)[C@H]2CCCN2C(=O)OC(C)(C)C)cc1]

The title compound (D7) (815 mg) was prepared according to the general procedure for amides preparation starting from (R)-1-(tert-butoxycarbonyl)pyrrolidine-2-carboxylic acid (500 mg, available from Sigma Aldrich #433818), and (S)-methyl 4-(1-aminoethyl)benzoate hydrochloride (501 mg). Reaction time: 18 hrs MS: (ES/+) m/z: 377 [MH$^+$] C20H28N2O5 requires 376.20

Chiral HPLC [Phenomenex Lux Cellulose-1; Mobile phase A: 70% n-hexane (+0.1% DEA), B: 30% EtOH; DAD: 254 nm]: Peak retention time: 7.93 min.

$^1$H NMR (400 MHz, CHCl3-d) δ (ppm): 8.00 (d, J=7.3 Hz, 2H), 7.80-7.53 (m, 1H), 7.35 (d, J=8.3 Hz, 2H), 5.15 (br. s., 1H), 4.35 (br. s., 1H), 3.93 (s, 3H), 3.37 (br. s., 2H), 2.07 (s, 4H), 1.50 (s, 12H).

General Procedure for Substituted Benzyl Amines Preparation

To a solution of selected cyclic amino-acid, cyclic amino-ester or cyclic amino-amide (1 eq) in ACN, Na$_2$CO$_3$ or Cs$_2$CO$_3$ (1.2-8 eq) and selected benzyl bromide (2 eq) were added sequentially and the resulting mixture was heated at 60-68° C. for 4-24 hrs or stirred at RT 18 hrs. After filtration of solids, the filtrate was evaporated in vacuo. The resulting residue was taken up in EtOAc and the organic phase was washed with water, dried over Na$_2$SO$_4$ and evaporated in vacuo. The crude material was purified on SPE-Si cartridge or Biotage SNAP-Si column eluting with mixtures of cHex/EtOAc or cHex/DCM or DCM/EtOAc affording the title substituted benzyl amine compound.

Description 8: (2R,4R)-3-(trifluoromethyl)benzyl 4-hydroxy-1-(3-(trifluoromethyl)benzyl)pyrrolidine-2-carboxylate (D8)

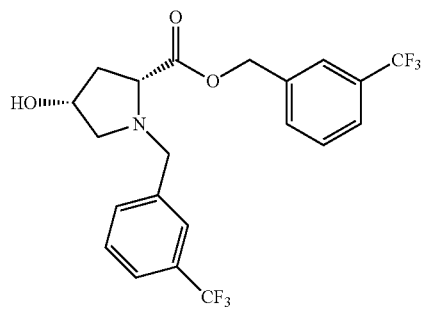 [SMILES: O=C(OCc1cccc(C(F)(F)F)c1)[C@H]1C[C@@H](O)CN1Cc1cccc(C(F)(F)F)c1]

The title compound (D8) (1.02 g) was prepared according to the general procedure for substituted benzyl amines preparation starting from cis-4-Hydroxy-D-proline (4.0 g; available from Aldrich#H5877) and 3-(Trifluoromethyl)benzyl bromide (9.37 ml). (Na$_2$CO$_3$: 2.5 eq; Reaction time: 24 hrs; 60° C.).

MS: (ES/+) m/z: 448.2 [MH$^+$] C21H19F6NO3 requires 447.13

$^1$H NMR (400 MHz, CHCl3-d) δ (ppm): 7.70-7.34 (m, 8H), 5.28-5.06 (m, 2H), 4.51 (br. s., 1H), 4.02 (d, J=13.3 Hz, 1H), 3.81-3.64 (m, 2H), 3.34 (dd, J=5.4, 10.1 Hz, 1H), 2.52 (dd, J=2.9, 10.1 Hz, 1H), 2.30 (td, J=7.0, 13.6 Hz, 1H), 2.23-2.10 (m, 1H), 1.76 (br. s., 1H).

Description 9: (2R,4S)-3-(trifluoromethyl)benzyl 4-fluoro-1-(3-(trifluoromethyl)benzyl)pyrrolidine-2-carboxylate (D9)

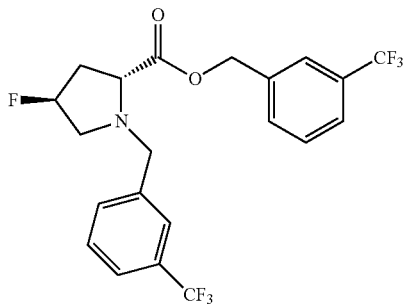 [SMILES: O=C(OCc1cccc(C(F)(F)F)c1)[C@H]1C[C@H](F)CN1Cc1cccc(C(F)(F)F)c1]

A solution of (2R,4R)-3-(trifluoromethyl)benzyl 4-hydroxy-1-(3-(trifluoromethyl)benzyl)pyrrolidine-2-carboxylate (D8) (200 mg, 0.45 mmol) in DCM (20 ml) cooled at −20° C. was treated with DAST (0.148 ml, 1.11 mmol) and the mixture was first stirred 1 h at −20° C. then 18 hrs at RT. The reaction was quenched with NaHCO$_3$ sat. sol. and the aqueous phase extracted with DCM (3×5 ml), dried over MgSO₄ and evaporated. The residue was purified by Biotage SNAP-Si column (25 g) eluting with petroleum ether/EtOAc from 90/10 to 80/20. Collected fractions, after solvent evaporation afforded the title compound (D9) (110 mg)

MS: (ES/+) m/z: 450.2 [MH⁺] C21H18F7NO2 requires 449.12

Chiral HPLC [Daicel OD-H; Mobile phase A: 80% n-hexane (+0.1% DEA); B: 20% IPA; DAD: 265 nm]: Peak retention time: 10.82 min.

¹H NMR (400 MHz, CHCl3-d) δ (ppm): 7.77-7.36 (m, 8H), 5.37-5.04 (m, 3H), 4.14 (d, J=13.3 Hz, 1H), 3.77-3.58 (m, 1H), 3.46 (br. s., 1H), 3.38-3.17 (m, 1H), 2.86-2.49 (m, 2H), 2.49-2.25 (m, 1H).

Description 10: (R)-methyl 2-methyl-1-(3-(trifluoromethyl)benzyl)pyrrolidine-2-carboxylate (D10)

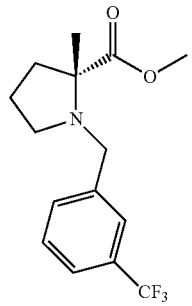 [SMILES: COC(=O)[C@@]1(C)CCCN1Cc1cccc(C(F)(F)F)c1]

The title compound (D10) (47 mg) was prepared according to the general procedure for substituted benzyl amines preparation starting from (R)-methyl 2-methylpyrrolidine-2-carboxylate hydrochloride (D3) (60 mg, 0.33 mmol) and 3-(Trifluoromethyl)benzyl bromide (0.076 ml, 0.50 mmol). (Na₂CO₃: 3 eq; Reaction time: 8 hrs; 60° C.).

MS: (ES/+) m/z: 302.2 [MH⁺] C15H18F3NO2 requires 301.13

General Procedure for t-Butyl Carbamate (Boc) Cleavage

To an ice cooled solution of Boc protected amine in DCM a 3:1 mixture TFA:DCM was added and the resulting mixture was stirred at RT 1 h prior evaporation of solvents. The residue was loaded onto SPE-SCX cartridge. The collected ammonia fractions after solvent evaporation afforded the title compounds.

Description 11: methyl 4-((1S)-1-(piperidine-2-carboxamido)ethyl) (diastereoisomers mixture) (D11)

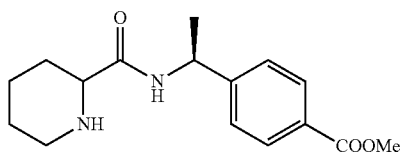

The title compound (D11) (1.37 g) was prepared according to the general procedure for t-Butyl carbamate (Boc) cleavage starting from tert-butyl 2-(((S)-1-(4-(methoxycarbonyl)phenyl)ethyl)carbamoyl)piperidine-1-carboxylate (D4) (1.95 g).

MS: (ES/+) m/z: 291.3 [MH⁺] C16H22N2O3 requires 290.16

¹H NMR (400 MHz, CHCl3-d) δ (ppm): 8.01 (d, 2H) 7.38 (d, 2H) 7.13-7.27 (m, 1H) 5.08-5.24 (m, 1H) 3.93 (s, 3H) 3.22-3.38 (m, 1H) 3.05 (d, 1H) 2.72 (t, 1H) 2.50 (br. s., 1H) 1.98 (d, 1H) 1.80 (d, 1H) 1.60 (br. s., 1H) 1.50 (d, 3H) 1.38-1.48 (m, 3H).

Description 12: methyl 4-((S)-1-((R)-piperidine-2-carboxamido)ethyl)benzoate (D12)

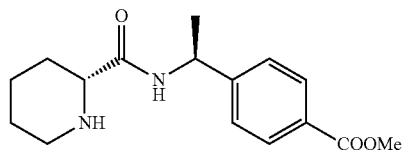 [SMILES: COC(=O)c1ccc([C@H](C)NC(=O)C2CCCCN2)cc1]

The title compound (D12) (286 mg) was prepared according to the general procedure for t-Butyl carbamate (Boc) cleavage starting from (R)-tert-butyl 2-(((S)-1-(4-(methoxycarbonyl)phenyl)ethyl)carbamoyl)piperidine-1-carboxylate (D5) (405 mg).

MS: (ES/+) m/z: 291.3 [MH⁺] C16H22N2O3 requires 290.16

Chiral HPLC [Phenomenex Lux Cellulose-1; Mobile phase A: 90% n-hexane (+0.1% DEA), B: 10% EtOH; DAD: 237 nm]: Peak retention time: 15.93 min.

¹H NMR (400 MHz, CHCl3-d) δ (ppm): 8.02 (d, 2H) 7.39 (d, 2H) 7.15 (d, 1H) 5.17 (t, 1H) 3.93 (s, 3H) 3.17-3.33 (m, 1H) 3.03 (d, 1H) 2.71 (br. s., 1H) 1.89-2.08 (m, 1H) 1.72-1.86 (m, 1H) 1.54-1.67 (m, 2H) 1.50 (d, 3H) 1.30-1.46 (m, 3H).

Description 13: (R)-methyl 4-(1-(piperidine-2-carboxamido)cyclopropyl)benzoate (D13)

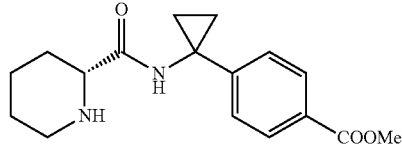 [SMILES: COC(=O)c1ccc(C2(NC(=O)[C@H]3CCCCN3)CC2)cc1]

The title compound (D13) (490 mg) was prepared according to the general procedure for t-Butyl carbamate (Boc) cleavage starting from (R)-tert-butyl 2-((1-(4-(methoxycarbonyl)phenyl)cyclopropyl)carbamoyl)piperidine-1-carboxylate (D6) (650 mg).

MS: (ES/+) m/z: 303.2 [MH⁺] C17H22N2O3 requires 302.16

Description 14: methyl 4-((S)-1-((R)-pyrrolidine-2-carboxamido)ethyl)benzoate (D14)

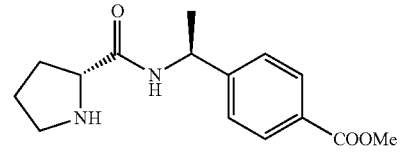 [SMILES: COC(=O)c1ccc([C@H](C)NC(=O)[C@H]2CCCN2)cc1]

The title compound (D14) (550 mg) was prepared according to the general procedure for t-Butyl carbamate (Boc) cleavage starting from (R)-tert-butyl 2-(((S)-1-(4-(methoxycarbonyl)phenyl)ethyl)carbamoyl)pyrrolidine-1-carboxylate (D7) (815 mg)

MS: (ES/+) m/z: 277.6 [MH$^+$] C15H20N2O3 requires 276.15

Chiral HPLC [Phenomenex Lux Cellulose-1; Mobile phase A: 70% n-hexane (+0.1% DEA), 30% EtOH; DAD: 240 nm]: Peak retention time: 8.65 min.

$^1$H NMR (400 MHz, CHCl3-d) δ (ppm): 8.00 (d, J=7.3 Hz, 2H), 7.80-7.53 (m, 1H), 7.35 (d, J=8.3 Hz, 2H), 5.15 (br. s., 1H), 4.35 (br. s., 1H), 3.93 (s, 3H), 3.37 (br. s., 2H), 2.07 (s, 4H), 1.50 (s, 12H).

General Procedure for Esters Hydrolysis

To a solution of the selected ester (1 eq) in dioxane/water (1:1), LiOH H$_2$O (1.2-4 eq) was added and the resulting mixture was stirred at RT. Organic solvent was evaporated off and the aqueous solution was washed with DCM and evaporated in vacuo. The residue was loaded on a C18 cartridge eluting with H$_2$O/MeOH 9/1 then MeOH. Collected methanolic phases were evaporated off affording the title compound as lithium salt.

Description 15: lithium (2R,4R)-4-hydroxy-1-(3-(trifluoromethyl)benzyl)pyrrolidine-2-carboxylate (D15)

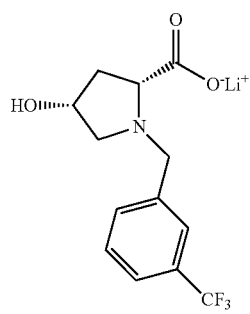

The title compound (D15) (16 mg) was prepared according to the general procedure for esters hydrolysis starting from (2R,4R)-3-(trifluoromethyl)benzyl 4-hydroxy-1-(3-(trifluoromethyl)benzyl)pyrrolidine-2-carboxylate (D8) (50 mg). (LiOH: 2 eq; Reaction time: 4 hrs).

MS: (ES/+) m/z: 290.2 [M-Li+2H$^+$] C13H13F3LiNO3 requires 295.10

$^1$H NMR (400 MHz, MeOH-d4) δ (ppm): 7.77 (br. s, 1H), 7.71-7.63 (m, 1H), 7.58-7.45 (m, 2H), 4.41-4.28 (m, 1H), 4.22-4.09 (m, 1H), 3.47-3.41 (m, 1H), 3.31-3.27 (m, 1H), 3.23-3.13 (m, 1H), 2.23-2.09 (m, 2H), 2.07-1.96 (m, 1H).

Description 16: lithium (2R,4S)-4-fluoro-1-(3-(trifluoromethyl)benzyl)pyrrolidine-2-carboxylate (D16)

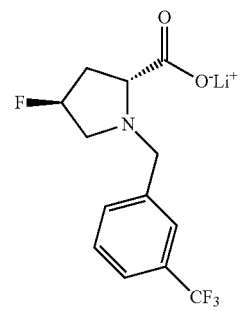

The title compound (D16) (60 mg) was prepared according to the general procedure for esters hydrolysis starting from (2R,4S)-3-(trifluoromethyl)benzyl 4-fluoro-1-(4-(trifluoromethyl)benzyl)pyrrolidine-2-carboxylate (D9) (110 mg). (LiOH: 2 eq; Reaction time: 18 hrs)

MS: (ES/+) m/z: 292.2 [M-Li+2H$^+$] C13H12F4LiNO2 requires 297.10

Description 17: lithium (R)-2-methyl-1-(3-(trifluoromethyl)benzyl)pyrrolidine-2-carboxylate (D17)

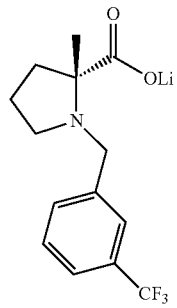

The title compound (D17) (37 mg) was prepared according to the general procedure for esters hydrolysis starting from (R)-methyl 2-methyl-1-(3-(trifluoromethyl)benzyl)pyrrolidine-2-carboxylate (D10) (47 mg). (LiOH: 2 eq; reaction time: 18 hrs).

MS: (ES/+) m/z: 288.3 [M-Li+2H$^+$] C14H15F3LiNO2 requires 293.21

Description 18: methyl 4-((1S)-1-(1-(3,4-difluorobenzyl)piperidine-2-carboxamido)ethyl)benzoate (diastereoisomer mixture) (D18)

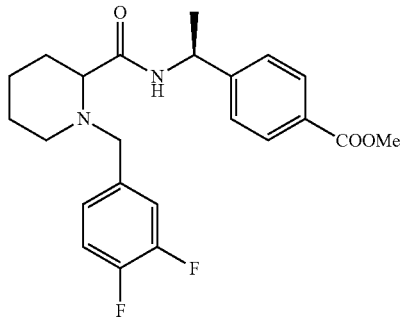 [SMILES: COC(=O)c1ccc([C@H](C)NC(=O)C2CCCCN2Cc2ccc(F)c(F)c2)cc1]

The title compound (D18) (67 mg) was prepared according to the general procedure for substituted benzyl amines preparation starting from methyl 4-((1S)-1-(piperidine-2-carboxamido)ethyl) (D11) (50 mg, 0.17 mmol) and 3,4-difluorobenzyl bromide (0.044 ml, 0.34 mmol). (Na$_2$CO$_3$: 2.5 eq; reaction time: 4 hrs; 68° C.)

MS: (ES/+) m/z: 417 [MH$^+$] C23H26F2N2O3 requires 416.19

Chiral HPLC [Phenomenex Lux Cellulose-1; Mobile phase A: 90% n-hexane (+0.1% DEA) 10% EtOH; DAD: 237 nm]: Peak 1 retention time: 17.94 min; Peak 2 retention time: 19.03.

$^1$H NMR (400 MHz, CHCl3-d) δ (ppm): 8.05 (d, J=8.0 Hz, 2H), 7.89 (d, J=7.9 Hz, 2H), 7.39 (d, J=7.9 Hz, 2H), 7.20-7.10 (m, 2H), 7.03 (d, J=8.8 Hz, 2H), 7.00-6.73 (m, 4H), 5.26-5.12 (m, 2H), 3.93 (d, J=8.1 Hz, 6H), 3.86 (d, J=14.1 Hz, 1H), 3.59 (d, J=14.2 Hz, 1H), 3.21 (d, J=14.1 Hz, 1H), 3.07 (d, J=14.2 Hz, 1H), 2.87 (br. s., 4H), 2.00 (d, J=12.8 Hz, 4H), 1.83-1.70 (m, 2H), 1.68-1.57 (m, J=12.3 Hz, 6H), 1.55 (d, J=6.9 Hz, 3H), 1.46 (d, J=6.8 Hz, 3H), 1.39-1.31 (m, 2H).

Description 19: methyl 4-((1S)-1-(1-(3-methylbenzyl)piperidine-2-carboxamido)ethyl)benzoate (diastereoisomers mixture) (D19)

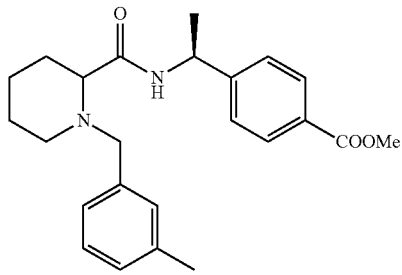 [SMILES: COC(=O)c1ccc([C@H](C)NC(=O)C2CCCCN2Cc2cccc(C)c2)cc1]

The title compound (D19) (63 mg) was prepared according to the general procedure for substituted benzyl amines preparation starting from methyl 4-((1S)-1-(piperidine-2-carboxamido)ethyl) (D11) (50 mg, 0.17 mmol) and 3-methyl benzyl bromide (0.046 ml, 0.34 mmol). (Na$_2$CO$_3$: 2.5 eq; reaction time: 3 hrs; 68° C.)

MS: (ES/+) m/z: 395.3 [MH$^+$] C24H30N2O3 requires 394.23

Description 20: methyl 4-((1S)-1-(1-(3-fluorobenzyl)piperidine-2-carboxamido)ethyl)benzoate (diastereoisomers mixture) (D20)

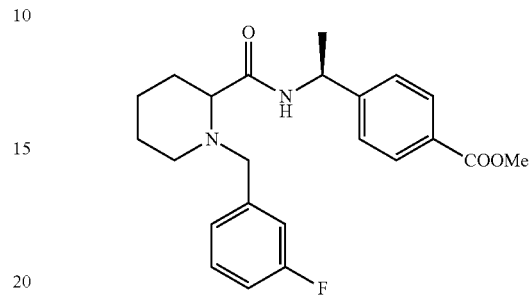

The title compound (D20) (54 mg) was prepared according to the general procedure for substituted benzyl amines preparation starting from methyl 4-((1S)-1-(piperidine-2-carboxamido)ethyl) (D11) (50 mg, 0.17 mmol) and 3-fluoro benzyl bromide (0.042 ml, 0.34 mmol). (Na$_2$CO$_3$: 2.5 eq; reaction time: 3 hrs; 68° C.)

MS: (ES/+) m/z: 399.3 [MH$^+$] C23H27FN2O3 requires 398.20

Description 21: methyl 4-((1S)-1-(1-(3-(trifluoromethyl)benzyl)piperidine-2-carboxamido)ethyl)benzoate (diastereoisomers mixture) (D21)

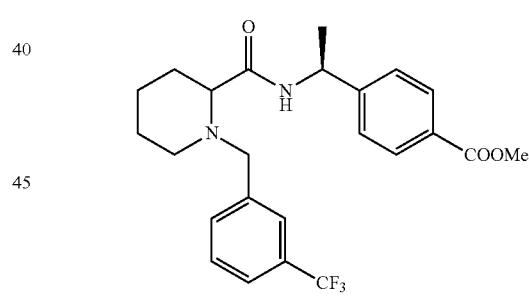

The title compound (D21) (45 mg) was prepared according to the general procedure for substituted benzyl amines preparation starting from methyl 4-((1S)-1-(piperidine-2-carboxamido)ethyl) (D11) (50 mg, 0.17 mmol) and 3-(trifluoromethyl)benzyl bromide (0.052 ml, 0.34 mmol). (Na$_2$CO$_3$: 2.5 eq; reaction time: 3 hrs; 68° C.)

MS: (ES/+) m/z: 449.3 [MH$^+$] C24H27F3N2O3 requires 448.20

$^1$H NMR (400 MHz, CHCl3-d) δ (ppm): 8.12-7.79 (m, 4H), 7.59 (d, J=13.4 Hz, 3H), 7.50 (br. s., 4H), 7.39 (d, J=8.2 Hz, 3H), 7.25 (d, J=8.0 Hz, 2H), 7.05 (d, J=7.9 Hz, 2H), 5.28-5.03 (m, 2H), 4.02-3.83 (m, 7H), 3.78-3.64 (m, J=14.3 Hz, 1H), 3.37-3.12 (m, 2H), 2.99-2.80 (m, 4H), 2.14-1.96 (m, 4H), 1.83-1.70 (m, J=13.0 Hz, 2H), 1.69-1.46 (m, 9H), 1.44 (d, J=6.9 Hz, 3H), 1.39-1.29 (m, 2H)

Description 22: methyl 4-((S)-1-((R)-1-(3-(trifluoromethyl)benzyl)piperidine-2-carboxamido)ethyl)benzoate (D22)

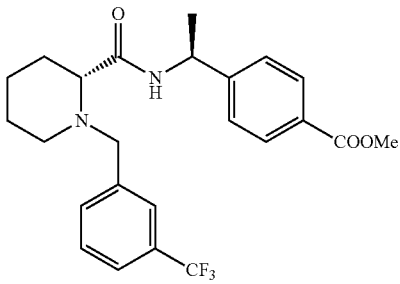 [SMILES: COC(=O)c1ccc([C@H](C)NC(=O)[C@H]2CCCCN2Cc2cccc(C(F)(F)F)c2)cc1]

The title compound (D22) (18 mg) was prepared according to the general procedure for substituted benzyl amines preparation starting from methyl 4-((S)-1-((R)-piperidine-2-carboxamido)ethyl)benzoate (D12) (40 mg, 0.14 mmol) and 3-(trifluoromethyl)benzyl bromide (0.031 ml, 0.21 mmol). ($Na_2CO_3$: 2.5 eq; reaction time: 4 hrs; 60° C.)

MS: (ES/+) m/z: 449.3 [MH$^+$] C24H27F3N2O3 requires 448.20

$^1$H NMR (400 MHz, CHCl3-d) δ (ppm): 8.04 (d, J=8.0 Hz, 2H), 7.64-7.54 (m, 2H), 7.50 (br. s., 2H), 7.39 (d, J=8.0 Hz, 2H), 7.05 (d, J=7.9 Hz, 1H), 5.17 (t, J=7.2 Hz, 1H), 3.98 (d, J=1.0 Hz, 1H), 3.94 (s, 3H), 3.31 (d, J=14.2 Hz, 1H), 3.00-2.81 (m, 2H), 2.10-1.95 (m, 2H), 1.81-1.69 (m, 1H), 1.63 (d, J=12.7 Hz, 1H), 1.57-1.46 (m, 2H), 1.44 (d, J=6.9 Hz, 3H), 1.32 (d, J=12.3 Hz, 1H).

Description 23: methyl 4-((S)-1-((R)-1-(3-fluorobenzyl)piperidine-2-carboxamido)ethyl)benzoate (D23)

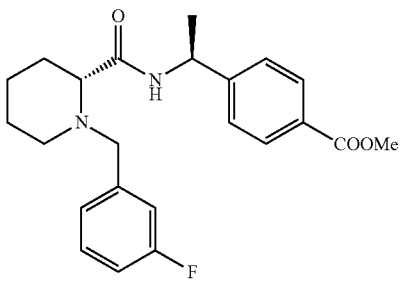 [SMILES: COC(=O)c1ccc([C@H](C)NC(=O)[C@H]2CCCCN2Cc2cccc(F)c2)cc1]

The title compound (D23) (40 mg) was prepared according to the general procedure for substituted benzyl amines preparation starting from methyl 4-((S)-1-((R)-piperidine-2-carboxamido)ethyl)benzoate (D12) (50 mg, 0.17 mmol) and 3-fluorobenzyl bromide (0.042 ml, 0.34 mmol). ($Na_2CO_3$: 2.5 eq; reaction time: 3 hrs; 60° C.)

MS: (ES/+) m/z: 399.3 [MH$^+$] C23H27FN2O3 requires 398.20

Description 24: methyl 4-((S)-1-((R)-1-(3-methylbenzyl)piperidine-2-carboxamido)ethyl)benzoate (D24)

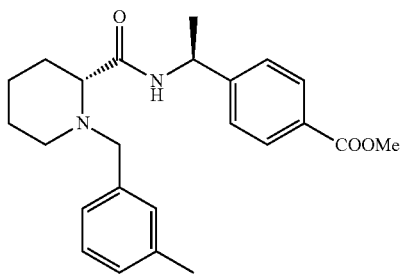 [SMILES: COC(=O)c1ccc([C@H](C)NC(=O)[C@H]2CCCCN2Cc2cccc(C)c2)cc1]

The title compound (D24) (48 mg) was prepared according to the general procedure for substituted benzyl amines preparation starting from methyl 4-((S)-1-((R)-piperidine-2-carboxamido)ethyl)benzoate (D12) (50 mg, 0.17 mmol) and 3-methylbenzyl bromide (0.046 ml, 0.34 mmol). ($Na_2CO_3$: 2.5 eq; reaction time: 3 hrs; 60° C.)

MS: (ES/+) m/z: 395.3 [MH$^+$] C24H30N2O3 requires 394.23

Description 25: methyl 4-((S)-1-((R)-1-(3-(trifluoromethoxy)benzyl)piperidine-2-carboxamido)ethyl)benzoate (D25)

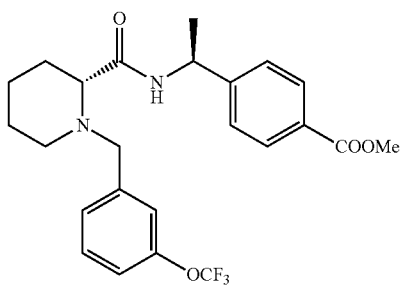 [SMILES: COC(=O)c1ccc([C@H](C)NC(=O)[C@H]2CCCCN2Cc2cccc(OC(F)(F)F)c2)cc1]

A mixture of methyl 4-((S)-1-((R)-piperidine-2-carboxamido)ethyl)benzoate (D12) (50 mg, 0.17 mmol) and 3-(trifluoromethoxy)benzaldehyde (0.025 ml, 0.20 mmol), NaBH(OAc)$_3$ (109 mg, 0.52 mmol) and catalytic $CH_3COOH$ in DCM (12 ml) was heated at 100° C. (2 cycles of 5 min each) under microwave irradiation. The resulting mixture was purified by SPE-Si (2 g) eluting with a mixture DCM/AcOEt from 100/0 to 80/20. Collected fractions after solvent evaporation afforded the title compound (D25) (52 mg).

MS: (ES/+) m/z: 395.3 [MH⁺] C24H27F3N2O4 requires 464.19

Description 26: (R)-methyl 4-(1-(1-(3-(trifluoromethyl)benzyl)piperidine-2-carboxamido)cyclopropyl)benzoate (D26)

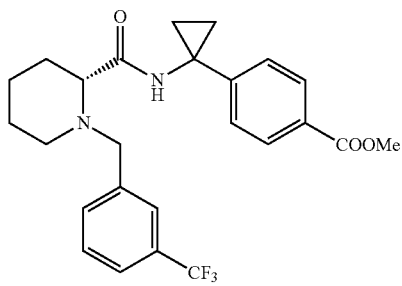 [SMILES: COC(=O)c1ccc(C2(NC(=O)[C@H]3CCCCN3Cc3cccc(C(F)(F)F)c3)CC2)cc1]

The title compound (D26) (76 mg) was prepared according to the general procedure for substituted benzyl amines preparation starting from (R)-methyl 4-(1-(piperidine-2-carboxamido)cyclopropyl)benzoate (D13) (50 mg, 0.16 mmol) and 3-(trifluoromethyl)benzyl bromide (0.038 ml, 0.25 mmol). (Na$_2$CO$_3$: 2.5 eq; reaction time: 6 hrs; 60° C.)

MS: (ES/+) m/z: 461.3 [MH⁺] C25H27F3N2O3 requires 460.20

Description 27: (R)-methyl 4-(1-(1-(3-methylbenzyl)piperidine-2-carboxamido)cyclopropyl)benzoate (D27)

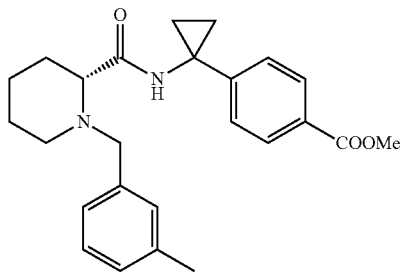 [SMILES: COC(=O)c1ccc(C2(NC(=O)[C@H]3CCCCN3Cc3cccc(C)c3)CC2)cc1]

The title compound (D27) (63 mg) was prepared according to the general procedure for substituted benzyl amines preparation starting from (R)-methyl 4-(1-(piperidine-2-carboxamido)cyclopropyl)benzoate (D13) (50 mg, 0.16 mmol) and 3-methyl benzyl bromide (0.033 ml, 0.25 mmol). (Na$_2$CO$_3$: 2.5 eq; reaction time: 6 hrs; 60° C.)

MS: (ES/+) m/z: 407.3 [MH⁺] C25H30N2O3 requires 406.23

Description 28: (R)-methyl 4-(1-(1-(3-fluorobenzyl)piperidine-2-carboxamido)cyclopropyl)benzoate (D28)

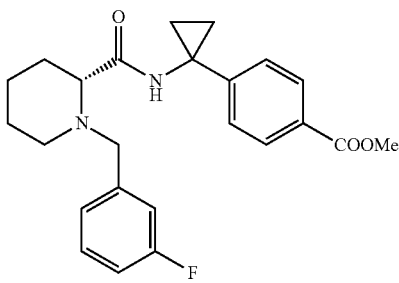 [SMILES: COC(=O)c1ccc(C2(NC(=O)[C@H]3CCCCN3Cc3cccc(F)c3)CC2)cc1]

The title compound (D28) (62 mg) was prepared according to the general procedure for substituted benzyl amines preparation starting from (R)-methyl 4-(1-(piperidine-2-carboxamido)cyclopropyl)benzoate (D13) (50 mg, 0.16 mmol) and 3-fluoro benzyl bromide (0.03 ml, 0.25 mmol). (Na$_2$CO$_3$: 2.5 eq; reaction time: 6 hrs; 60° C.)

MS: (ES/+) m/z: 411.3 [MH⁺] C24H27FN2O3 requires 410.20

Description 29: (R)-methyl 4-(1-(1-(4-fluoro-3-methylbenzyl)piperidine-2-carboxamido)cyclopropyl)benzoate (D29)

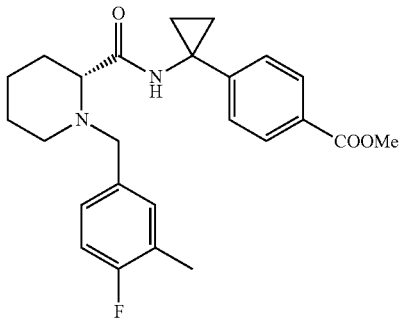 [SMILES: COC(=O)c1ccc(C2(NC(=O)[C@H]3CCCCN3Cc3ccc(F)c(C)c3)CC2)cc1]

A mixture of (R)-methyl 4-(1-(piperidine-2-carboxamido)cyclopropyl)benzoate (D13) (40 mg, 0.13 mmol) and 4-fluoro-3-methyl benzaldehyde (0.02 ml, 0.16 mmol), NaBH(OAc)$_3$ (84 mg, 0.4 mmol) and CH$_3$COOH (0.076 ml, 1.3 mmol) in DCM (10 ml) was heated at 110° C. (2 cycles of 5 min each) under microwave irradiation. The resulting mixture was purified by SPE-Si (2 g) eluting with a mixture DCM/AcOEt from 100/0 to 80/20. Collected fractions after solvent evaporation afforded the title compound (D29) (33 mg).

MS: (ES/+) m/z: 425.3 [MH+] C25H29FN2O3 requires 424.22

Description 30: (R)-methyl 4-(1-(1-(4-fluoro-3-(trifluoromethyl)benzyl)piperidine-2-carboxamido)cyclopropyl)benzoate (D30)

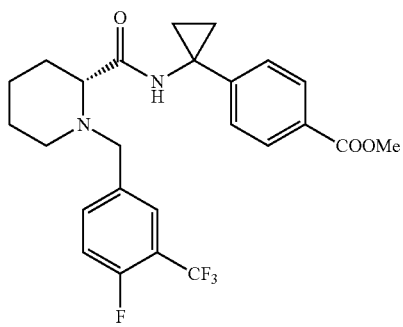 [SMILES: COC(=O)c1ccc(C2(NC(=O)[C@H]3CCCCN3Cc3ccc(F)c(C(F)(F)F)c3)CC2)cc1]

The title compound (D30) (35 mg) was prepared according sperimental procedure described in description 29 starting from (R)-methyl 4-(1-(piperidine-2-carboxamido)cyclopropyl)benzoate (D13) (40 mg, 0.13 mmol) and 4-fluoro-3-(trifluoromethyl)benzaldehyde (0.02 ml, 0.16 mmol)

MS: (ES/+) m/z: 479.3 [MH+] C25H26F4N2O3 requires 478.19

Description 31: methyl 4-((S)-1-((R)-1-(3-fluorobenzyl)pyrrolidine-2-carboxamido)ethyl)benzoate (D31)

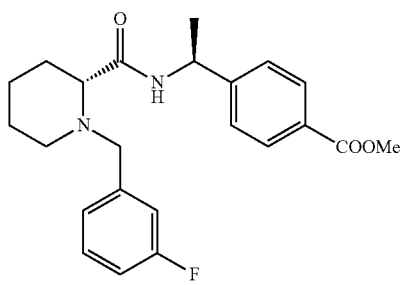

The title compound (D31) (55 mg) was prepared according to the general procedure for substituted benzyl amines preparation starting from methyl 4-((S)-1-((R)-pyrrolidine-2-carboxamido)ethyl)benzoate (D14) (50 mg, 0.18 mmol) and 3-fluoro benzyl bromide (0.044 ml, 0.36 mmol). (Na2CO3: 2.5 eq; reaction time: 5 hrs; 70° C.)

MS: (ES/+) m/z: 385.6 [MH+] C22H25FN2O3 requires 384.18

Description 32: methyl 4-((S)-1-((R)-1-(3-(trifluoromethyl)benzyl)pyrrolidine-2-carboxamido)ethyl)benzoate (D32)

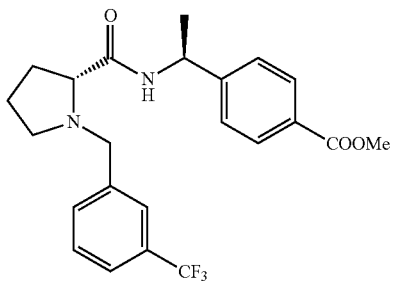 [SMILES: COC(=O)c1ccc([C@H](C)NC(=O)[C@H]2CCCN2Cc2cccc(C(F)(F)F)c2)cc1]

The title compound (D32) (70 mg) was prepared according to the general procedure for substituted benzyl amines preparation starting from methyl 4-((S)-1-((R)-pyrrolidine-2-carboxamido)ethyl)benzoate (D14) (50 mg, 0.18 mmol) and 3-(trifluoromethyl)benzyl bromide (0.055 ml, 0.36 mmol). (Na2CO3: 2.5 eq; reaction time: 5 hrs; 70° C.)

MS: (ES/+) m/z: 434.9 [MH+] C23H25F3N2O3 requires 434.18

Description 33: methyl 4-((S)-1-((R)-1-(3-methylbenzyl)pyrrolidine-2-carboxamido)ethyl)benzoate (D33)

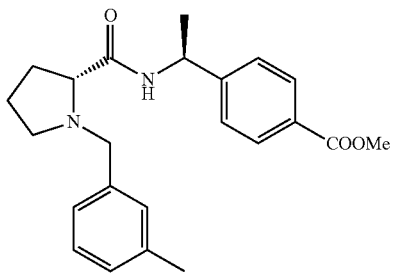 [SMILES: COC(=O)c1ccc([C@H](C)NC(=O)[C@H]2CCCN2Cc2cccc(C)c2)cc1]

The title compound (D33) (30 mg) was prepared according to the general procedure for substituted benzyl amines preparation starting from methyl 4-((S)-1-((R)-pyrrolidine-2-carboxamido)ethyl)benzoate (D14) (50 mg, 0.18 mmol) and 3-methylbenzyl bromide (0.05 ml, 0.36 mmol). (Na2CO3: 2.5 eq; reaction time: 5 hrs; 70° C.)

MS: (ES/+) m/z: 381.6 [MH+] C23H28N2O3 requires 380.21

Description 34: methyl 4-((S)-1-((R)-1-(3,4-difluorobenzyl)pyrrolidine-2-carboxamido)ethyl)benzoate (D34)

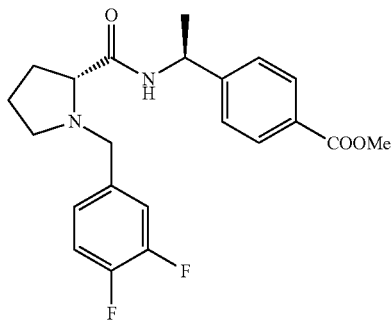 [SMILES: COC(=O)c1ccc([C@H](C)NC(=O)[C@H]2CCCN2Cc2ccc(F)c(F)c2)cc1]

The title compound (D34) (39 mg) was prepared according to the general procedure for substituted benzyl amines preparation starting from methyl 4-((S)-1-((R)-pyrrolidine-2-carboxamido)ethyl)benzoate (D14) (50 mg, 0.18 mmol) and 3,4-difluorobenzyl bromide (0.046 ml, 0.36 mmol). ($Na_2CO_3$: 2.5 eq; reaction time: 5 hrs; 70° C.)

MS: (ES/+) m/z: 403.6 [MH$^+$] C22H24F2N2O3 requires 402.18

Description 35: methyl 4-((S)-1-((2R,4R)-4-hydroxy-1-(3-(trifluoromethyl)benzyl)pyrrolidine-2-carboxamido)ethyl)benzoate (D35)

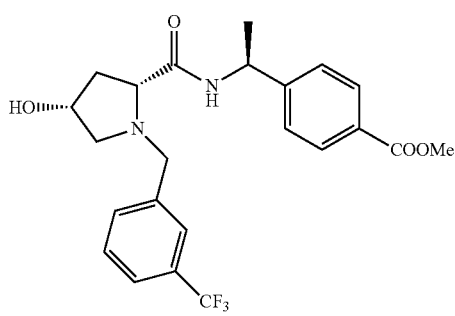 [SMILES: COC(=O)c1ccc([C@H](C)NC(=O)[C@H]2C[C@@H](O)CN2Cc2cccc(C(F)(F)F)c2)cc1]

The title compound (D35) (10.3 mg) was prepared according to the general procedure for amides preparation starting from lithium (2R,4R)-4-hydroxy-1-(3-(trifluoromethyl)benzyl)pyrrolidine-2-carboxylate (D15) (11.7 mg, 0.054 mmol) and methyl 4-(1-aminocyclopropyl)benzoate hydrochloride (27.2 mg, 0.054 mmol).

MS: (ES/+) m/z: 451.2 [MH$^+$] C23H25F3N2O4 requires 450.18

$^1$H NMR (400 MHz, CHCl3-d) δ (ppm): 8.02 (d, J=8.0 Hz, 2H), 7.64-7.55 (m, 2H), 7.50 (d, J=3.9 Hz, 3H), 7.33 (d, J=8.0 Hz, 2H), 5.14-5.00 (m, J=7.1, 7.1 Hz, 1H), 4.40 (br. s., 1H), 4.01 (d, J=13.3 Hz, 1H), 3.93 (s, 3H), 3.79 (d, J=13.1 Hz, 1H), 3.65 (br. s., 1H), 3.31 (d, J=6.1 Hz, 1H), 2.58 (d, J=8.2 Hz, 1H), 2.37-2.20 (m, 1H), 2.10-1.92 (m, 2H), 1.41 (d, J=6.8 Hz, 3H).

Description 36: methyl 4-((S)-1-((2R,4S)-4-fluoro-1-(3-(trifluoromethyl)benzyl)pyrrolidine-2-carboxamido)ethyl)benzoate (D36)

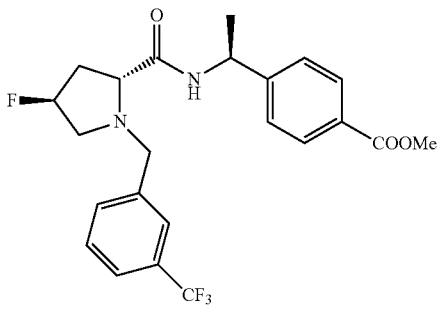

The title compound (D36) (67.3 mg) was prepared according to the general procedure for amides preparation starting from lithium (2R,4S)-4-fluoro-1-(3-(trifluoromethyl)benzyl)pyrrolidine-2-carboxylate (D16) (60 mg) and (S)-methyl 4-(1-aminoethyl)benzoate hydrochloride (43.5 mg).

MS: (ES/+) m/z: 475.2 [MH+Na$^+$]C23H24F4N2O3 requires 452.17

$^1$H NMR (400 MHz, CHCl3-d) δ (ppm): 8.01 (d, J=8.1 Hz, 2H), 7.75-7.46 (m, 5H), 7.36 (d, J=8.1 Hz, 2H), 5.32-5.00 (m, 2H), 4.01 (d, J=13.2 Hz, 1H), 3.92 (s, 3H), 3.70 (d, J=13.2 Hz, 1H), 3.54-3.33 (m, 2H), 2.73-2.41 (m, 2H), 2.31-2.11 (m, 1H), 1.42 (d, J=6.8 Hz, 3H)

Description 37: methyl 4-((S)-1-((R)-2-methyl-1-(3-(trifluoromethyl)benzyl)pyrrolidine-2-carboxamido)ethyl)benzoate (D37)

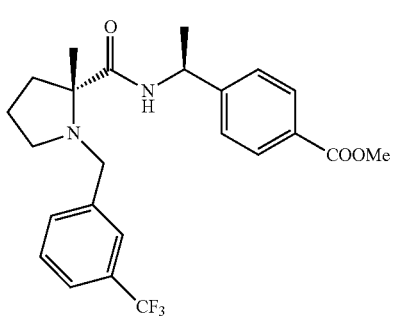 [SMILES: COC(=O)c1ccc([C@H](C)NC(=O)[C@@]2(C)CCCN2Cc2cccc(C(F)(F)F)c2)cc1]

The title compound (D37) (30.9 mg) was prepared according to the general procedure for amides preparation starting from lithium (R)-2-methyl-1-(3-(trifluoromethyl)benzyl)pyrrolidine-2-carboxylate (D17) (37 mg, 0.13 mmol) and methyl 4-(1-aminocyclopropyl)benzoate hydrochloride (27.2 mg, 0.13 mmol).

MS: (ES/+) m/z: 449.3 [MH$^+$] C24H27F3N2O3 requires 448.20

$^1$H NMR (400 MHz, CHCl3-d) δ (ppm): 8.02 (d, J=8.0 Hz, 2H), 7.99 (br. s., 1H), 7.64-7.55 (m, 2H), 7.50 (d, J=4.1 Hz, 2H), 7.37 (d, J=7.9 Hz, 2H), 5.19-5.06 (m, J=7.2, 7.2 Hz, 1H), 3.93 (s, 4H), 3.46 (d, J=13.1 Hz, 1H), 3.07-2.93 (m, 1H), 2.46 (d, J=6.8 Hz, 1H), 2.09-1.95 (m, 1H), 1.85-1.77 (m, 2H), 1.75-1.65 (m, 1H), 1.51 (d, J=6.9 Hz, 3H), 1.37 (br. s., 3H).

EXAMPLES

Example 1 lithium 4-((1S)-1-(1-(3,4-difluorobenzyl)piperidine-2-carboxamido) ethyl)benzoate (E1)

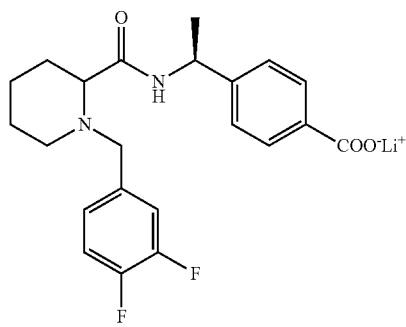

The title compound (E1) (62 mg) was prepared according to the general procedure for esters hydrolysis starting from methyl 4-((1S)-1-(1-(3,4-difluorobenzyl)piperidine-2-carboxamido)ethyl)benzoate (D18) (67 mg). (LiOH H$_2$O: 1.75 eq; reaction time: 3 hrs)

MS: (ES/+) m/z: 403 [M-Li+2H$^+$] C22H23F2LiN2O3 requires 408.18

$^1$H NMR (400 MHz, MeOH-d4) δ (ppm): 7.92 (d, J=7.9 Hz, 1H), 7.87 (d, J=7.9 Hz, 1H), 7.36 (d, J=8.0 Hz, 1H), 7.34-7.22 (m, J=8.0 Hz, 2H), 7.22-6.98 (m, 2H), 5.19-5.04 (m, 1H), 3.70 (t, J=1.0 Hz, 1H), 3.41-3.35 (m, 1H), 3.10 (t, J=1.0 Hz, 1H), 2.90-2.76 (m, 2H), 2.04-1.92 (m, 1H), 1.90-1.65 (m, 3H), 1.64-1.58 (m, 1H), 1.49 (dd, J=6.9, 18.5 Hz, 3H), 1.40-1.26 (m, 1H)

Example 2 lithium 4-((1S)-1-(1-(3-methylbenzyl)piperidine-2-carboxamido) ethyl)benzoate (E2)

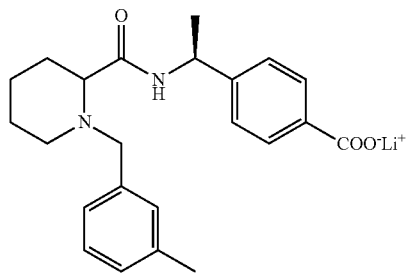

The title compound E2 (60 mg) was prepared according to the general procedure for esters hydrolysis starting from methyl 4-((1S)-1-(1-(3-methylbenzyl)piperidine-2-carboxamido)ethyl)benzoate (D19) (42 mg). (LiOH H$_2$O: 1.75 eq; reaction time: 3 hrs)

MS: (ES/+) m/z: 381.3 [M-Li+2H$^+$] C23H27LiN2O3 requires 386.22

Example 3 lithium 4-((1S)-1-(1-(3-fluorobenzyl)piperidine-2-carboxamido) ethyl)benzoate (E3)

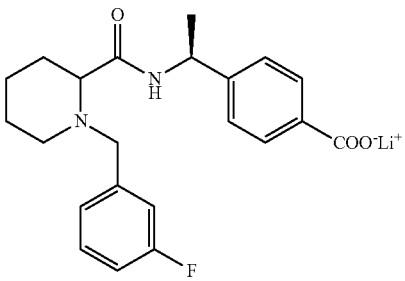

The title compound (E3) (50 mg) was prepared according to the general procedure for esters hydrolysis starting from methyl 4-((1S)-1-(1-(3-fluorobenzyl)piperidine-2-carboxamido)ethyl)benzoate (D20) (54 mg). (LiOH H$_2$O: 1.75 eq; reaction time: 3 hrs)

MS: (ES/+) m/z: 385.3 [M-Li+2H$^+$] C22H24FLiN2O3 requires 390.19

Example 4 lithium 4-((1S)-1-(1-(3-(trifluoromethyl)benzyl)piperidine-2-carboxamido)ethyl)benzoate (E4)

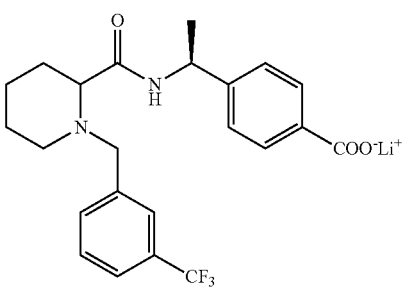

The title compound (E4) (20 mg) was prepared according to the general procedure for esters hydrolysis starting from methyl 4-((1S)-1-(1-(3-(trifluoromethyl)benzyl)piperidine-2-carboxamido)ethyl)benzoate (D21) (45 mg). (LiOH H$_2$O: 1.75 eq; reaction time: 3 hrs)

MS: (ES/+) m/z: 435.3 [M-Li+2H$^+$] C23H24F3LiN2O3 requires 440.19

$^1$H NMR (400 MHz, MeOH-d4) δ (ppm): 7.97-7.82 (m, 2H), 7.74-7.63 (m, 1H), 7.63-7.46 (m, 3H), 7.39-7.28 (m, 2H), 5.16-5.07 (m, 1H), 3.88-3.75 (m, 1H), 3.27-3.12 (m, 2H), 2.91-2.79 (m, 2H), 2.07-1.93 (m, 1H), 1.91-1.65 (m, 3H), 1.64-1.58 (m, 1H), 1.53-1.44 (m, 3H), 1.42-1.29 (m, 1H).

Example 5 lithium 4-((S)-1-((R)-1-(3-(trifluoromethyl)benzyl) piperidine-2-carboxamido)ethyl)benzoate (E5)

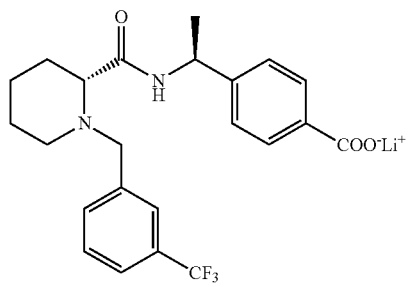

The title compound (E5) (5.02 mg) was prepared according to the general procedure for esters hydrolysis starting from methyl 4-((S)-1-((R)-1-(3-(trifluoromethyl)benzyl)piperidine-2-carboxamido)ethyl)benzoate (D22) (19 mg). (LiOH H$_2$O: 1.75 eq; reaction time: 3 hrs)

MS: (ES/+) m/z: 435.2 [M-Li+2H$^+$] C23H24F3LiN2O3 requires 440.19

$^1$H NMR (400 MHz, MeOH-d4) δ (ppm): 7.93 (d, J=7.9 Hz, 2H), 7.61 (d, J=1.0 Hz, 2H), 7.54 (d, J=1.0 Hz, 2H), 7.36 (d, J=7.9 Hz, 2H), 5.16-5.03 (m, 1H), 3.88-3.80 (m, 1H), 3.27 (d, J=1.0 Hz, 1H), 2.86 (d, J=10.3 Hz, 2H), 2.07-1.96 (m, 1H), 1.93-1.65 (m, 3H), 1.65-1.51 (m, 2H), 1.46 (d, J=6.9 Hz, 3H), 1.41-1.27 (m, 1H).

Example 6 lithium 4-((S)-1-((R)-1-(3-fluorobenzyl)piperidine-2-carboxamido)ethyl)benzoate (E6)

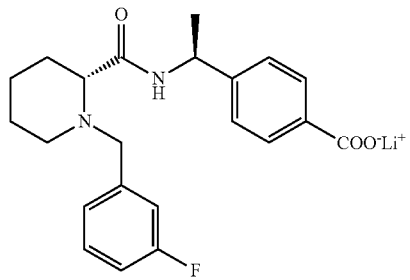

The title compound (E6) (36 mg) was prepared according to the general procedure for esters hydrolysis starting from methyl 4-((S)-1-((R)-1-(3-fluorobenzyl)piperidine-2-carboxamido)ethyl)benzoate (D23 (40 mg). (LiOH H$_2$O: 3 eq; reaction time: 3 hrs)

MS: (ES/+) m/z: 385.3 [M-Li+2H$^+$] C22H24FLiN2O3 requires 390.19

Chiral HPLC [Daicel OD-H; Mobile phase A: 60% n-hexane (+0.2% TFA), 40% EtOH; DAD: 235 nm]: Peak retention time: 5.7 min.

$^1$H NMR (400 MHz, MeOH-d4) δ (ppm): 7.93 (d, J=7.9 Hz, 2H), 7.41-7.26 (m, 3H), 7.20-6.92 (m, 3H), 5.09 (d, J=6.9 Hz, 1H), 3.78 (d, J=13.4 Hz, 1H), 3.18 (d, J=13.4 Hz, 1H), 2.86 (dd, J=11.3, 17.0 Hz, 2H), 2.07-1.94 (m, J=2.8 Hz, 1H), 1.91-1.64 (m, 3H), 1.63-1.53 (m, 2H), 1.47 (d, J=6.9 Hz, 3H), 1.41-1.26 (m, J=11.6 Hz, 1H).

Example 7 lithium 4-((S)-1-((R)-1-(3-methylbenzyl)piperidine-2-carboxamido) ethyl)benzoate (E7)

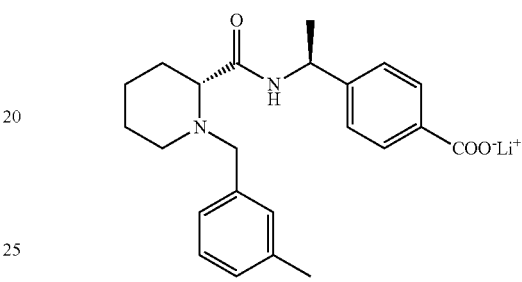

The title compound (E7) (28 mg) was prepared according to the general procedure for esters hydrolysis starting from methyl 4-((S)-1-((R)-1-(3-methylbenzyl)piperidine-2-carboxamido)ethyl)benzoate (D24) (48 mg). (LiOH H$_2$O: 3 eq; reaction time: 3 hrs)

MS: (ES/+) m/z: 381.3 [M-Li+2H$^+$] C23H27LiN2O3 requires 386.22

Chiral HPLC [Daicel IC; Mobile phase A: 70% n-hexane (+0.2% TFA), 30% EtOH; DAD: 235 nm]: Peak retention time: 6.6 min.

Example 8 lithium 4-((S)-1-((R)-1-(3-(trifluoromethoxy)benzyl) piperidine-2-carboxamido)ethyl)benzoate (E8)

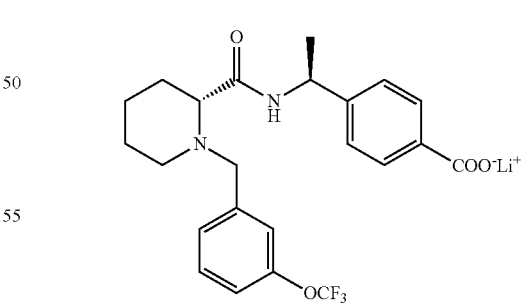

The title compound (E8) (51 mg) was prepared according to the general procedure for esters hydrolysis starting from methyl 4-((S)-1-((R)-1-(3-(trifluoromethoxy)benzyl)piperidine-2-carboxamido)ethyl)benzoate (D25) (52 mg). (LiOH H$_2$O: 3 eq; reaction time: 3 hrs)

MS: (ES/+) m/z: 451.3 [M-Li+2H$^+$] C23H24F3LiN2O4 requires 456.18

Example 9 lithium (R)-4-(1-(1-(3-(trifluoromethyl)benzyl)piperidine-2-carboxamido)cyclopropyl)benzoate (E9)

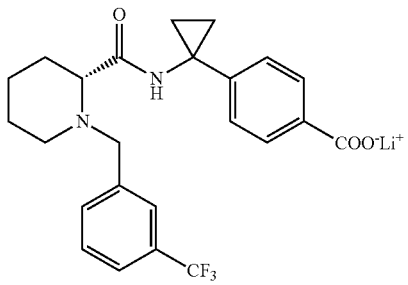

The title compound (E9) (51 mg) was prepared according to the general procedure for esters hydrolysis starting from (R)-methyl 4-(1-(1-(3-(trifluoromethyl)benzyl)piperidine-2-carboxamido)cyclopropyl)benzoate (D26) (76 mg). (LiOH H$_2$O: 3 eq; reaction time: 3 hrs)

MS: (ES/+) m/z: 447.2 [M-Li+2H$^+$] C24H24F3LiN2O3 requires 452.19

Chiral HPLC [Daicel OD-H; Mobile phase A: 90% n-hexane (+0.1% TFA), 10% IPA; DAD: 225 nm]: Peak retention time: 26.9 min.

$^1$H NMR (400 MHz, MeOH-d4) δ (ppm): 7.86 (d, J=1.0 Hz, 2H), 7.71 (s, 1H), 7.67-7.61 (m, 1H), 7.60-7.55 (m, 1H), 7.55-7.48 (m, 1H), 7.23 (d, J=1.0 Hz, 2H), 3.81 (d, J=1.0 Hz, 1H), 3.26-3.19 (m, 2H), 2.90-2.79 (m, 2H), 2.06-1.97 (m, 1H), 1.96-1.89 (m, 1H), 1.85-1.75 (m, 2H), 1.64-1.53 (m, 2H), 1.43-1.26 (m, 4H).

Example 10 lithium (R)-4-(1-(1-(3-methylbenzyl)piperidine-2-carboxamido)cyclopropyl)benzoate (E10)

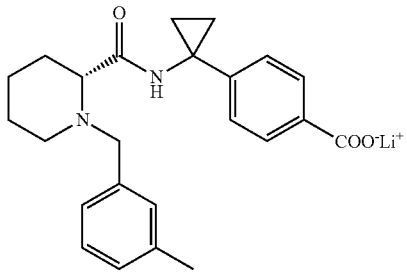

The title compound (E10) (61 mg) was prepared according to the general procedure for esters hydrolysis starting from (R)-methyl 4-(1-(1-(3-methylbenzyl)piperidine-2-carboxamido)cyclopropyl)benzoate (D27) (63 mg). (LiOH H$_2$O: 3 eq; reaction time: 3 hrs)

MS: (ES/+) m/z: 393.2 [M-Li+2H$^+$] C24H27LiN2O3 requires 398.22

$^1$H NMR (400 MHz, MeOH-d4) δ (ppm): 7.86 (d, J=8.0 Hz, 2H), 7.32-7.03 (m, 6H), 3.74 (d, J=13.1 Hz, 1H), 3.38-3.30 (1H, 1H, under residual solvent), 3.12 (d, J=13.1 Hz, 1H), 2.90 (d, J=11.5 Hz, 1H), 2.79 (d, J=10.2 Hz, 1H), 2.34 (s, 3H), 2.02-1.87 (m, 2H), 1.84-1.67 (m, 2H), 1.66-1.48 (m, 2H), 1.44-1.26 (m, 4H).

Example 11 lithium (R)-4-(1-(1-(3-fluorobenzyl)piperidine-2-carboxamido)cyclopropyl)benzoate (E11)

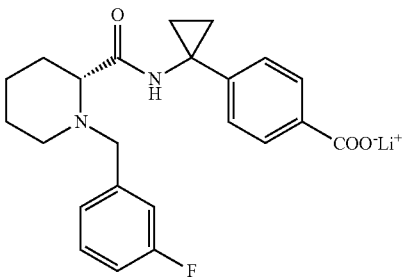

The title compound (E11) (61 mg) was prepared according to the general procedure for esters hydrolysis starting from (R)-methyl 4-(1-(1-(3-fluorobenzyl)piperidine-2-carboxamido)cyclopropyl)benzoate (D28) (62 mg). (LiOH H$_2$O: 3 eq; reaction time: 3 hrs)

MS: (ES/+) m/z: 397.2 [M-Li+2H$^+$] C23H24FLiN2O3 requires 402.19

Example 12

(R)-4-(1-(1-(4-fluoro-3-methylbenzyl)piperidine-2-carboxamido)cyclopropyl)benzoic acid (E12)

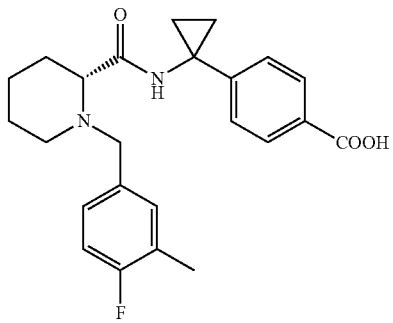 [SMILES: Cc1cc(CN2CCCC[C@@H]2C(=O)NC2(c3ccc(C(=O)O)cc3)CC2)ccc1F]

The title compound (E12) (10.1 mg) was prepared according to the general procedure for esters hydrolysis starting from (R)-methyl 4-(1-(1-(4-fluoro-3-methylbenzyl)piperidine-2-carboxamido)cyclopropyl)benzoate (D29) (33 mg). (LiOH H$_2$O: 3 eq; reaction time: 3 hrs)

MS: (ES/+) m/z: 411.2 [MH$^+$] C24H27FN2O3 requires 410.20

$^1$H NMR (400 MHz, MeOH-d4) δ (ppm): 7.90 (d, J=7.8 Hz, 2H), 7.29 (d, J=7.8 Hz, 2H), 7.24 (d, J=7.0 Hz, 1H), 7.17 (br. s., 1H), 6.98 (s, 1H), 3.76 (d, J=13.1 Hz, 1H), 3.39-3.36 (1H, under residual solvent), 3.20 (d, J=13.1 Hz, 1H), 3.02-

2.86 (m, 2H), 2.27 (s, 3H), 2.17-2.03 (m, 1H), 1.97-1.91 (m, 1H), 1.79 (d, J=8.6 Hz, 2H), 1.68-1.49 (m, 2H), 1.44-1.29 (m, 4H)

Example 13 lithium (R)-4-(1-(1-(4-fluoro-3-(trifluoromethyl)benzyl)piperidine-2-carboxamido)cyclopropyl)benzoate (E13)

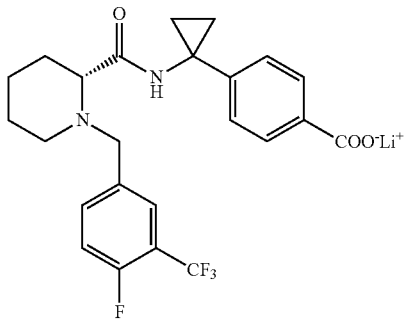

The title compound (E13) (11.1 mg) was prepared according to the general procedure for esters hydrolysis starting from (R)-methyl 4-(1-(1-(4-fluoro-3-(trifluoromethyl)benzyl)piperidine-2-carboxamido)cyclopropyl)benzoate (D30) (35 mg). (LiOH H$_2$O: 3 eq; reaction time: 3 hrs)

MS: (ES/+) m/z: 465.2 [M-Li+2H$^+$] C24H23F4LiN2O3 requires 470.18

Example 14 lithium 4-((S)-1-((R)-1-(3-fluorobenzyl)pyrrolidine-2-carboxamido)ethyl)benzoate (E14)

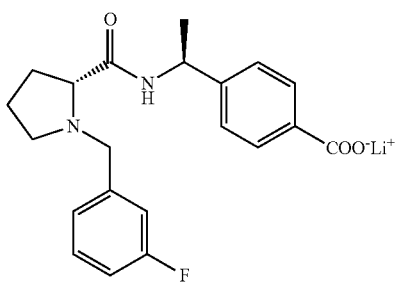

The title compound (E14) (48 mg) was prepared according to the general procedure for esters hydrolysis starting from methyl 4-((S)-1-((R)-1-(3-fluorobenzyl)pyrrolidine-2-carboxamido)ethyl)benzoate (D31) (53 mg). (LiOH H$_2$O: 1.5 eq; reaction time: 24 hrs)

MS: (ES/+) m/z: 371.5 [M-Li+2H$^+$] C24H23F4LiN2O3 requires 376.18

Example 15 lithium 4-((S)-1-((R)-1-(3-(trifluoromethyl)benzyl)pyrrolidine-2-carboxamido)ethyl)benzoate (E15)

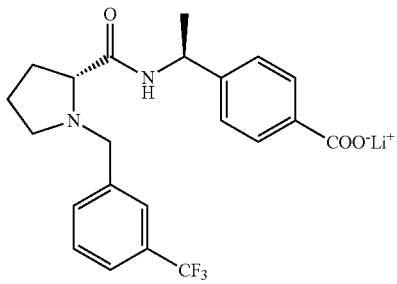

The title compound (E15) (57 mg) was prepared according to the general procedure for esters hydrolysis starting from methyl 4-((S)-1-((R)-1-(3-(trifluoromethyl)benzyl)pyrrolidine-2-carboxamido)ethyl)benzoate (D32) (69 mg). (LiOH H$_2$O: 1.5 eq; reaction time: 24 hrs)

MS: (ES/+) m/z: 421.6 [M-Li+2H$^+$] C22H22F3LiN2O3 requires 426.17

Chiral HPLC [Daicel OD-H; Mobile phase A: 90% n-hexane (+0.5% TFA), 10% EtOH; DAD: 235 nm]: Peak retention time: 12.5 min.

$^1$H NMR (400 MHz, MeOH-d4) δ (ppm): 7.92 (d, J=7.9 Hz, 2H), 7.70 (s, 1H), 7.67-7.51 (m, 3H), 7.28 (d, J=7.9 Hz, 2H), 4.98-4.89 (m, 1H), 3.88 (d, J=1.0 Hz, 1H), 3.75 (d, J=1.0 Hz, 1H), 3.27-3.19 (m, 1H), 3.19-3.09 (m, 1H), 2.56-2.45 (m, 1H), 2.30-2.12 (m, 1H), 1.82 (br. s., 3H), 1.36 (d, J=6.9 Hz, 3H).

Example 16 lithium 4-((S)-1-((R)-1-(3-methylbenzyl)pyrrolidine-2-carboxamido)ethyl)benzoate (E16)

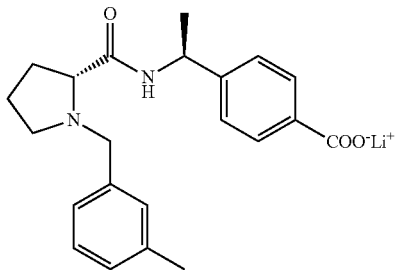

The title compound (E16) (24 mg) was prepared according to the general procedure for esters hydrolysis starting from methyl 4-((S)-1-((R)-1-(3-methylbenzyl)pyrrolidine-2-carboxamido)ethyl)benzoate (D33) (29 mg). (LiOH H$_2$O: 1.5 eq; reaction time: 24 hrs)

MS: (ES/+) m/z: 367.6 [M-Li+2H⁺] C22H25LiN2O3 requires 372.20

Example 17 lithium 4-((S)-1-((R)-1-(3,4-difluorobenzyl)pyrrolidine-2-carboxamido)ethyl)benzoate (E17)

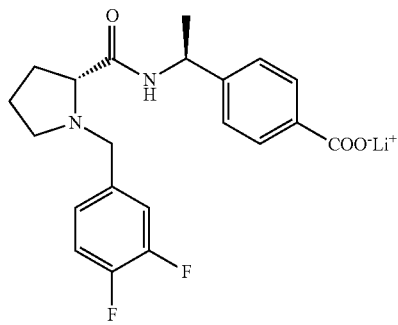

The title compound (E17) (36 mg) was prepared according to the general procedure for esters hydrolysis starting from methyl 4-((S)-1-((R)-1-(3,4-difluorobenzyl)pyrrolidine-2-carboxamido)ethyl)benzoate (D34) (38 mg). (LiOH H₂O: 1.5 eq; reaction time: 24 hrs)

MS: (ES/+) m/z: 389.6 [M-Li+2H⁺] C21H21F2LiN2O3 requires 394.17

Chiral HPLC [Daicel OD-H; Mobile phase A: 90% n-hexane (+0.5% TFA), 10% EtOH; DAD: 237 nm]: Peak retention time: 15.7 min.

¹H NMR (400 MHz, MeOH-d4) δ (ppm): 7.93 (d, J=7.9 Hz, 2H), 7.30 (d, J=7.8 Hz, 3H), 7.26-7.07 (m, 2H), 5.03-4.89 (m, 1H), 3.74 (s, 1H), 3.67 (s, 1H), 3.24-3.09 (m, 2H), 2.56-2.41 (m, 1H), 2.30-2.10 (m, 1H), 1.86-1.71 (m, J=2.5 Hz, 3H), 1.40 (d, J=6.9 Hz, 3H)

Example 18 lithium 4-((S)-1-((R)-2-methyl-1-(3-(trifluoromethyl)benzyl)pyrrolidine-2-carboxamido)ethyl)benzoate (E18)

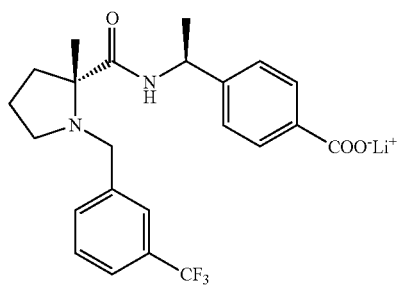

The title compound (E18) (9 mg) was prepared according to the general procedure for esters hydrolysis starting from methyl 4-((S)-1-((R)-2-methyl-1-(3-(trifluoromethyl)benzyl)pyrrolidine-2-carboxamido)ethyl)benzoate (D35) (68.6 mg). (LiOH H₂O: 2 eq; reaction time: 18 hrs)

MS: (ES/+) m/z: 435.3 [M-Li+2H⁺] C23H24F3LiN2O3 requires 440.19

¹H NMR (400 MHz, MeOH-d4) δ (ppm): 7.94 (d, J=7.9 Hz, 2H), 7.71-7.64 (m, 2H), 7.63-7.55 (m, 2H), 7.31 (d, J=7.9 Hz, 2H), 5.06-4.97 (m, J=6.9 Hz, 1H), 3.96 (d, J=13.5 Hz, 1H), 3.56 (d, J=13.5 Hz, 1H), 3.05-2.96 (m, 1H), 2.58-2.49 (m, J=7.9 Hz, 1H), 2.12-2.00 (m, 1H), 1.88-1.71 (m, 3H), 1.49 (d, J=6.9 Hz, 3H), 1.36 (s, 3H).

Example 19 lithium 4-((S)-1-((2R,4R)-4-hydroxy-1-(3-(trifluoromethyl)benzyl)pyrrolidine-2-carboxamido)ethyl)benzoate (E19)

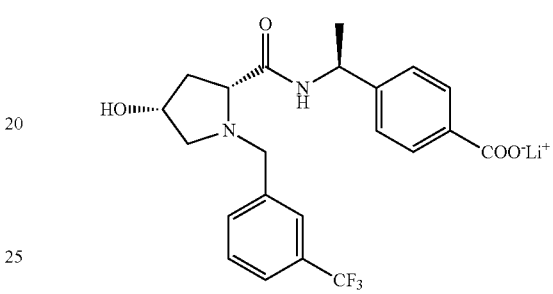

The title compound (E19) (9 mg) was prepared according to the general procedure for esters hydrolysis starting from methyl 4-((S)-1-((2R,4R)-4-hydroxy-1-(3-(trifluoromethyl)benzyl)pyrrolidine-2-carboxamido)ethyl)benzoate (D36) (10.3 mg). (LiOH H₂O: 2 eq; reaction time: 18 hrs)

MS: (ES/+) m/z: 437.3 [M-Li+2H⁺] C22H22F3LiN2O4 requires 442.17

¹H NMR (400 MHz, MeOH-d4) δ (ppm): 7.92 (d, J=7.9 Hz, 2H), 7.70 (br. s., 1H), 7.61 (br. s., 2H), 7.56-7.50 (m, 1H), 7.29 (d, J=7.9 Hz, 2H), 4.99-4.92 (m, 1H), 4.40-4.27 (m, 1H), 3.94 (d, J=1.0 Hz, 1H), 3.78 (d, J=1.0 Hz, 1H), 3.50 (t, J=1.0 Hz, 1H), 3.31-3.26 (m, 1H), 2.49 (t, J=1.0 Hz, 1H), 2.20-2.08 (m, 1H), 2.04-1.94 (m, 1H), 1.38 (d, J=6.9 Hz, 3H).

Example 20 lithium 4-((S)-1-((2R,4S)-4-fluoro-1-(3-(trifluoromethyl)benzyl)pyrrolidine-2-carboxamido)ethyl)benzoate (E20)

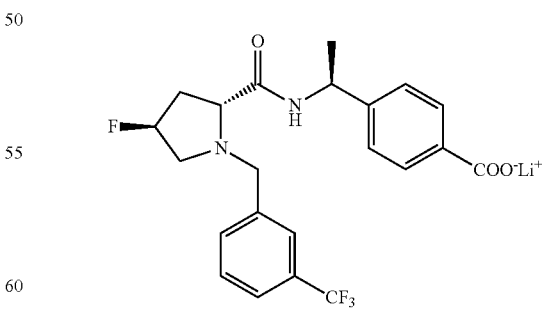

The title compound (E20) (50 mg) was prepared according to the general procedure for esters hydrolysis starting from methyl 4-((S)-1-((2R,4S)-4-fluoro-1-(3-(trifluoromethyl)benzyl)pyrrolidine-2-carboxamido)ethyl)benzoate (D37) (67.3 mg). (LiOH H₂O: 2 eq; reaction time: 18 hrs)

MS: (ES/+) m/z: 439.2 [M-Li+2H$^+$] C22H21F4LiN2O3 requires 444.16

$^1$H NMR (400 MHz, MeOH-d4) δ (ppm): 7.90 (d, J=7.9 Hz, 2H), 7.71 (s, 1H), 7.69-7.54 (m, 3H), 7.27 (d, J=7.9 Hz, 2H), 5.28-5.05 (m, 1H), 4.92-4.90 (m, 1H), 3.92 (d, J=1.0 Hz, 1H), 3.83 (d, J=1.0 Hz, 1H), 3.38 (br. s., 2H), 2.83-2.48 (m, 2H), 2.17-1.97 (m, 1H), 1.34 (d, J=6.9 Hz, 3H).

Example 21

Determination of In Vitro Effects of the Invention Compounds

Stable Expression of Human EP$_4$ Receptors in the Human Embryonic Kidney (HEK293) Cell Line The cDNA clone of human EP$_4$ receptor (NM_000958.2) was obtained from Invitrogen™: Ultimate™ ORF Clone Collection-Clone ID IOH46525. The coding sequence was subcloned in expression vector pcDNATM6.2/V5-DEST by Gateway technology (Invitrogen™).

Human embryonic kidney cells (HEK-293) were stably transfected with expression vector for human EP$_4$ receptor in according to the method described in FuGENE®6 Transfection Reagent's manual (Roche Applied Science®).

Preparation of Membrane Fraction:

The EP$_4$ transfected cells were grown in Dulbecco's modified Eagle's medium containing 10% fetal bovine serum and 10 μg/ml Blasticidin S HCl (selection medium) at 37° C. in a humidified atmosphere of 5% CO2 in air.

For the membrane preparation, cells in flask were harvested by hypotonical/mechanical lysis with chilled (4° C.) TE buffer (5 mM TRIS, 5 mM etylenediamine tetra-acetic acid (EDTA), pH 7.4).

Cells were detached and lysed with 10 ml of hypotonic lysis buffer and by scraping. The cell lysate was vortexed for 30 sec and centrifuged at 40000×g at 4° C. for 22 min.

a) Membrane Binding Assay[3H]-Prostaglandin E2

The membrane pellet was resuspended in the same buffer (5 mM TRIS, 5 mM ethylenediamine tetra-acetic acid (EDTA), pH 7.4), and protein concentration was determined by Bradford method (Bio-Bad® assay).

This membrane preparation was stored at −80° C. freezer until use for binding assay.

([$^3$H]-PGE$_2$) membranes binding assays toward hEP$_4$ receptors (human EP$_4$/HEK293 transfectant, see above) and hEP$_2$ receptors (human EP$_2$/HEK293 transfectant, purchased from PerkinElmer Inc) were performed in 10 mM MES-KOH buffer pH6, containing 10 mM MgCl$_2$ and 1 mM CaCl$_2$ for EP$_4$ binding assay or 50 mM Tris-Cl, BSA 0.5% for EP$_2$ binding assay (according to supplier indication).

Ten microgram of protein from membrane fractions were incubated in a total volume of 0.1 ml (EP$_4$) or 0.2 ml (EP$_2$) with 1 nM (EP$_4$) or 3 nM (EP$_2$) [$^3$H]-PGE$_2$ (PerkinElmer Inc, 171 Ci/mmol). In both assays to determine the total binding or non specific binding, 1% DMSO or 1 μM prostaglandin E$_2$ (EP$_4$) or 100 μM (EP$_2$) were added to reaction mixtures, respectively. Incubation was conducted in a polypropylene 96 multiwell for 90 min (EP$_4$) or 60 min (EP$_2$) at room temperature prior to separation of the bound and free radioligand by vacuum manifold rapid filtration on glass fiber filters (Unifilter GFB96, PerkinElmer Inc) pre-soaked in 0.3% polyethyleneimine. Filters were washed with ice cold buffer pH 7.4 (50 mM HEPES, NaCl 500 mM, BSA 0.1% for EP$_4$ binding assay or 50 mM Tris-Cl for EP$_2$ binding assays) and the residual [$^3$H]-PGE$_2$ binding determined by solid scintillation counter (TopCount, PerkinElmer Inc).

In standard competition experiments the compounds were tested in a concentration range from 1 nM to 1 μM, and IC$_{50}$ determined. The affinity (Ki) of each compound was calculated according to the Cheng-Prousoff equation: Ki=IC50/ (1+([C]/Kd)). Results were expressed as pKi (−log 10 Ki (M)

Compounds of example 1 to 20 were tested according to method of example 21a in a final concentration range range from 1 nM to 1 μM. All compounds showed good to excellent EP$_4$ affinities having pKi values from 6.3 to 8.4 at EP$_4$ receptor.

b) cAMP Assay on Human EP$_4$ Membrane of Transfected Cells.

The assay is based on the competition between endogenous cAMP and exogenously added biotinylated cAMP. The capture of cAMP is achieved by using a specific antibody conjugated to Donor beads.

Cell membranes prepared as described above, were resuspended in 1 ml stimulation buffer (HBSS 1×+BSA 0.1%+ IBMX 0.5 mM+HEPES 5 mM+MgCl$_2$ 10 mM+GTP 1 nM+GDP 10 μM+ATP 100 μM-pH 7.4). Cell membranes were dispensed into white 384-well microplates at final concentration of 1 μg/well and used for the determination of cAMP with the alphascreen cAMP functional assay (EnVision-PerkinElmer). Cell membrane/anti-cAMP Acceptor beads mix (5 μl) and a mixture of analysed compounds (dissolved in 100% DMSO to a final maximal concentration of 0.01% DMSO)/PGE$_2$ (5 μl) were incubated at room temperature (22-23° C.) for 30 min in the dark. The Biotinylated-cAMP and donor beads (15 μl) were dispensed into each well to start the competition reaction. After 1 h incubation RT (22-23° C.) in the dark the plate was read using EnVision platform to determine the cAMP level (excitation: 680 nm; emission:520,620 nm).

In each experiment:

cAMP standard curve (concentration range from 1×10-6 to 1×10-11 M in log intervals) with a negative control (no cAMP)

a positive control:forskolin 10 μM

Antagonism studies were performed stimulating HEK293 cell membrane with PGE$_2$ 3 nM. The AlphaScreen signal is plotted as a function of log concentration of cAMP and EC50 is determined. EC50 value is calculated by linear regression.

Some compounds were tested according to method of example 21b. All compounds showed good to excellent EP$_4$ antagonism having EC50 values from 300 nM to 0.1 nM at EP$_4$ receptor.

The results of membrane binding assay and cAMP assay on human EP$_4$ membrane of transfected cells selection of preferred compounds are summarised in table 1.

TABLE 1

| Example | Binding pKi | EC50 (nM) |
| --- | --- | --- |
| E5 | 7.5 | 1.0 |
| E9 | 8.1 | 2.9 |
| E12 | 7.5 | 6.0 |
| E13 | 8 | 8.0 |
| E15 | 7.7 | 13.5 |
| E19 | 7.4 | 0.1 |

The invention claimed is:
1. A cyclic amine derivative of Formula (I)

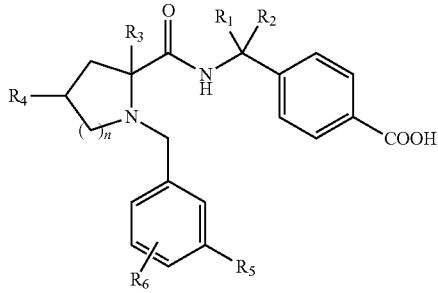

or a pharmaceutically acceptable salt or derivative thereof, wherein:

$R_1$ and $R_2$ are independently hydrogen, linear or branched $C_{1-3}$ alkyl or joined together they form a cyclopropyl ring;

n is 1 or 2, $R_3$ is hydrogen or a linear or branched $C_{1-3}$ alkyl, $R_4$ is hydrogen, fluorine, or hydroxy group, $R_5$ is halogen, cyano, linear or branched $C_{1-3}$ alkyl, trifluoromethyl or trifluoromethoxy, $R_6$ is hydrogen or halogen.

2. A cyclic amine derivative of Formula (I) according to claim 1, wherein the halogen in $R_5$ is fluorine.

3. A cyclic amine derivative of Formula (I) according to claim 1, wherein the linear or branched $C_{1-3}$ alkyl is methyl.

4. A cyclic amine derivative of Formula (I) according to claim 1, wherein n is 1.

5. A cyclic amine derivative of Formula (I) according to claim 4, wherein $R_1$ is hydrogen, $R_2$ is methyl, $R_3$ is hydrogen, $R_4$ is hydrogen, fluorine or hydroxy, $R_5$ is fluorine, trifluoromethyl or methyl, $R_6$ is hydrogen.

6. A cyclic amine derivative of Formula (I) according to claim 5, wherein $R_4$ is hydrogen.

7. A cyclic amine derivative of Formula (I) according to claim 1, wherein n is 2.

8. A cyclic amine derivative of Formula (I) according to claim 7, wherein $R_1$ is hydrogen, $R_2$ is methyl, $R_3$ is hydrogen, $R_4$ is hydrogen, $R_5$ is fluorine, trifluoromethyl, methyl or trifluoromethoxy, $R_6$ is hydrogen.

9. A cyclic amine derivative of Formula (I) according to claim 1 selected from the group consisting of: lithium 4-((S)-1-((R)-1-(3-(trifluoromethyl)benzyl)piperidine-2-carboxamido)ethyl) benzoate, lithium (R)-4-(1-(1-(3-(trifluoromethyl)benzyl) piperidine-2-carboxamido) cyclopropyl) benzoate, (R)-4-(1-(1-(4-fluoro-3-methylbenzyl)piperidine-2-carboxamido)cyclopropyl) benzoic acid, lithium (R)-4-(1-(1-(4-fluoro-3-(trifluoromethyl)benzyl)piperidine-2-carboxamido) cyclopropyl)benzoate, lithium 4-((S)-1-((R)-1-(3-(trifluoromethyl)benzyl)pyrrolidine-2-carboxamido) ethyl)benzoate; and lithium 4-((S)-1-((2R,4R)-4-hydroxy-1-(3-(trifluoromethyl)benzyl)pyrrolidine-2-carboxamido) ethyl) benzoate.

10. A pharmaceutical composition comprising a compound of Formula (I) according to claim 1 or a pharmaceutically acceptable salt thereof and a pharmaceutically acceptable carrier and/or excipient.

11. A method of treatment of a disease selected from the group consisting of: pain, inflammation, glaucoma, osteoporosis and ulcerative colitis, comprising the administration of an effective amount of a compound of Formula (I) according to claim 1.

* * * * *